United States Patent
Watson et al.

(10) Patent No.: US 8,632,971 B2
(45) Date of Patent: *Jan. 21, 2014

(54) METHODS AND MATERIALS FOR DETERMINING THE EFFICACY OF PROSTATE CANCER THERAPIES

(75) Inventors: James Douglas Watson, Kohimaramara (NZ); Richard Llewellyn Sydney Forster, Pukekohe (NZ); Damian Jay White, Kingsland (NZ)

(73) Assignee: Caldera Health Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,048

(22) Filed: Aug. 30, 2012

(65) Prior Publication Data

US 2013/0116140 A1     May 9, 2013

Related U.S. Application Data

(63) Continuation-in-part of application No. 13/291,994, filed on Nov. 8, 2011, now abandoned.

(51) Int. Cl.
C12Q 1/68      (2006.01)
C07K 16/00     (2006.01)
G01N 33/573    (2006.01)

(52) U.S. Cl.
USPC .................. 435/6.1; 435/7.4; 530/387.1

(58) Field of Classification Search
None
See application file for complete search history.

(56) References Cited

U.S. PATENT DOCUMENTS

| 5,525,473 | A | 6/1996 | Hill et al. |
| 5,928,878 | A | 7/1999 | Allard et al. |
| 6,632,624 | B1 | 10/2003 | Degorce et al. |
| 6,835,822 | B1 | 12/2004 | Hubert et al. |
| 7,569,356 | B2 | 8/2009 | Afar et al. |
| 7,914,988 | B1 * | 3/2011 | Chudin et al. ............... 435/6.11 |
| 2003/0108963 | A1 | 6/2003 | Schlegel et al. |
| 2011/0306514 | A1 | 12/2011 | Hewitt et al. |

FOREIGN PATENT DOCUMENTS

| WO | 2008/039774 A1 | 4/2008 |
| WO | 2008067065 A2 | 6/2008 |
| WO | 2011127219 A1 | 10/2011 |

OTHER PUBLICATIONS

Zhu et al., Protein chip technology, Current Opinion in Chemical Biology, 2003, 7:55-63.*
Tomlins et al., Recurrent Fusion of TMPRSS2 and ETS Transcription Factor Genes in Prostate Cancer, Science, Oct. 28, 2005 vol. 310.*
Bonner et al., "Prostatic" serum acid phosphatase level in cancer of the prostate, JAMA, vol. 164, No. 10, Jul. 1957.*
Lehrer et al., C-reactive protein is significantly associated with prostate-specific antigen and metastatic disease in prostate cancer, 2005, BJU International, 95, 961-962.*

(Continued)

*Primary Examiner* — Jim Ketter
*Assistant Examiner* — Reza Ghafoorian
(74) *Attorney, Agent, or Firm* — Janet Sleath; Speckman Law Group PLLC

(57) ABSTRACT

Methods for monitoring, and determining the efficacy of, a treatment for prostate cancer in a subject are provided, such methods including detecting the levels of expression of multiple polypeptide biomarkers in biological samples obtained from the subject prior to, and during, a course of treatment. Specific patterns of changes in the expression of the polypeptide biomarkers are indicative of the effectiveness of the treatment in the subject.

8 Claims, 9 Drawing Sheets

(56) References Cited

OTHER PUBLICATIONS

Madu, Chikezie O. et al., "Novel diagnostic biomarkers for prostate cancer," Journal of Cancer, vol. 1, pp. 150-177 (Oct. 6, 2010).

Beer, Thomas M. et al., "Double-Blinded Randomized Study of High-Dose Calcitriol Plus Docetaxel Compared With Placebo Plus Docetaxel in Androgen-Independent Prostate Cancer: A Report From the ASCENT Investigators," Journal of Clinical Oncology, vol. 25, No. 6, pp. 669-674 (2007).

Berruti, A et al., "Independent prognostic role of circulating chromogranin A in prostate cancer patients with hormone-refractory disease," Endocrine-Related Cancer, vol. 12, pp. 109-117 (2005).

Castelli, Tommaso et al., "Molecular markers for prostate cancer," Frontiers in Bioscience, Elite Edition, vol. 2, pp. 641-656 (Jan. 1, 2010).

Lorente, J.A. et al., "Clinical Efficacy of Bone Alkaline Phosphatase and Prostate Specific Antigen in the Diagnosis of Bone Metastasis in Prostate Cancer," The Journal of Urology, vol. 155, pp. 1348-1351 (Apr. 1996).

Ramirez, M.L. et al., "Beyond Prostate-Specific Antigen: Alternate Serum Markers," Prostate Cancer Prostatic Dis., vol. 11, No. 3, pp. 216-229 (2008).

Sardana, G. et al., "Emerging Biomarkers for Diagnosis and Prognosis of Prostate Cancer," Clinical Chemistry, vol. 54, No. 12, pp. 1951-1960 (2008).

Xu, Weihong et al., "Human transcription array for high-throughput clinical studies," Proc. Natl. Acad. Sci. USA, vol. 108, No. 9, pp. 3207-3712 (Mar. 1, 2011).

\* cited by examiner

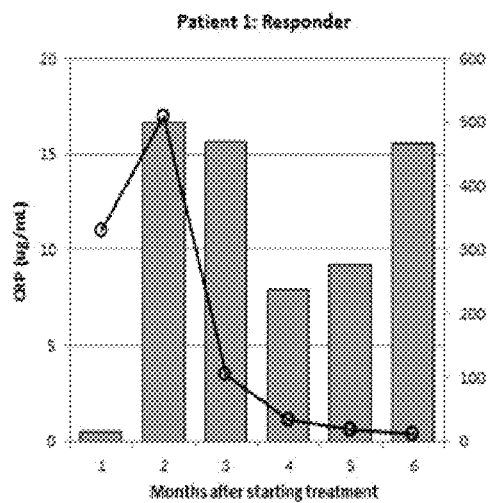 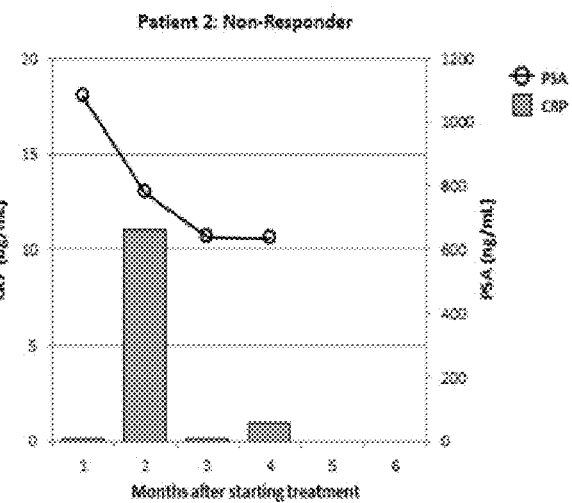
Figure 5A　　　　　　　　　Figure 5B
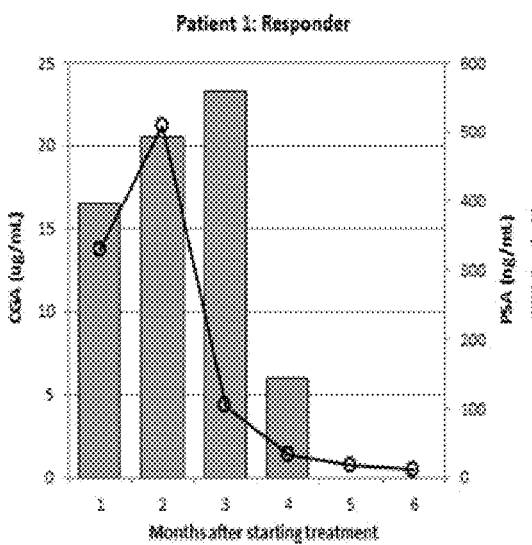 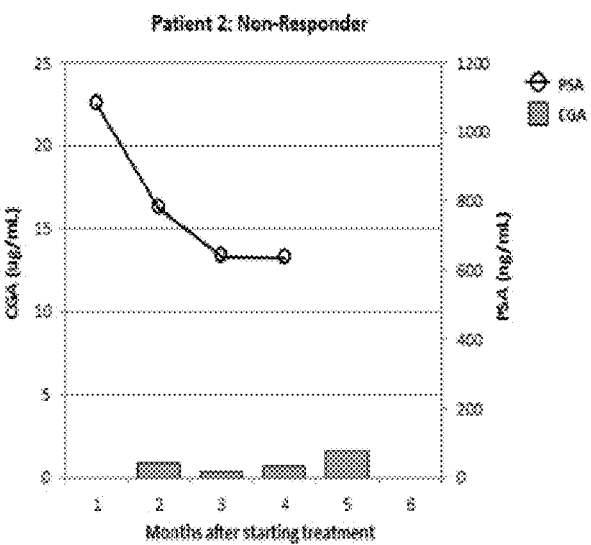
Figure 6A　　　　　　　　　Figure 6B

SEQUENCE LISTING

<160> NUMBER OF SEQ ID NOS: 20

<210> SEQ ID NO 1
<211> LENGTH: 261
<212> TYPE: PRT
<213> ORGANISM: Homo sapiens

<400> SEQUENCE: 1

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 2
<211> LENGTH: 69
<212> TYPE: PRT
<213> ORGANISM: Homo sapiens

<400> SEQUENCE: 2

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

```
Val Cys Gly Gly Val Leu Val His Pro Gln Trp Val Leu Thr Ala Ala
 50                  55                  60

His Cys Ile Arg Lys
 65
```

<210> SEQ ID NO 3
<211> LENGTH: 218
<212> TYPE: PRT
<213> ORGANISM: Homo sapiens

<400> SEQUENCE: 3

```
Met Trp Val Pro Val Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
             20                  25                  30

Lys His Ser Gln Pro Trp Gln Val Leu Val Ala Ser Arg Gly Arg Ala
         35                  40                  45

Val Cys Gly Gly Val Leu Val His Pro Gln Trp Val Leu Thr Ala Ala
 50                  55                  60

His Cys Ile Arg Lys Pro Gly Asp Asp Ser Ser His Asp Leu Met Leu
 65                  70                  75                  80

Leu Arg Leu Ser Glu Pro Ala Glu Leu Thr Asp Ala Val Lys Val Met
             85                  90                  95

Asp Leu Pro Thr Gln Glu Pro Ala Leu Gly Thr Thr Cys Tyr Ala Ser
            100                 105                 110

Gly Trp Gly Ser Ile Glu Pro Glu Glu Phe Leu Thr Pro Lys Lys Leu
        115                 120                 125

Gln Cys Val Asp Leu His Val Ile Ser Asn Asp Val Cys Ala Gln Val
130                 135                 140

His Pro Gln Lys Val Thr Lys Phe Met Leu Cys Ala Gly Arg Trp Thr
145                 150                 155                 160

Gly Gly Lys Ser Thr Cys Ser Gly Asp Ser Gly Gly Pro Leu Val Cys
                165                 170                 175

Asn Gly Val Leu Gln Gly Ile Thr Ser Trp Gly Ser Glu Pro Cys Ala
            180                 185                 190

Leu Pro Glu Arg Pro Ser Leu Tyr Thr Lys Val Val His Tyr Arg Lys
        195                 200                 205

Trp Ile Lys Asp Thr Ile Val Ala Asn Pro
        210                 215
```

<210> SEQ ID NO 4
<211> LENGTH: 238
<212> TYPE: PRT
<213> ORGANISM: Homo sapiens

<400> SEQUENCE: 4

```
Met Trp Val Pro Val Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
             20                  25                  30

Lys His Ser Gln Pro Trp Gln Val Leu Val Ala Ser Arg Gly Arg Ala
         35                  40                  45

Val Cys Gly Gly Val Leu Val His Pro Gln Trp Val Leu Thr Ala Ala
 50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
```

-continued

```
                    85                  90                  95
Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
            130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
                180                 185                 190

Thr Lys Phe Met Leu Cys Ala Gly Arg Trp Thr Gly Gly Lys Ser Thr
                195                 200                 205

Cys Ser Trp Val Ile Leu Ile Thr Glu Leu Thr Met Pro Ala Leu Pro
            210                 215                 220

Met Val Leu His Gly Ser Leu Val Pro Trp Arg Gly Val
225                 230                 235

<210> SEQ ID NO 5
<211> LENGTH: 457
<212> TYPE: PRT
<213> ORGANISM: Homo sapiens

<400> SEQUENCE: 5

Met Arg Ser Ala Ala Val Leu Ala Leu Leu Leu Cys Ala Gly Gln Val
1               5                   10                  15

Thr Ala Leu Pro Val Asn Ser Pro Met Asn Lys Gly Asp Thr Glu Val
            20                  25                  30

Met Lys Cys Ile Val Glu Val Ile Ser Asp Thr Leu Ser Lys Pro Ser
        35                  40                  45

Pro Met Pro Val Ser Gln Glu Cys Phe Glu Thr Leu Arg Gly Asp Glu
    50                  55                  60

Arg Ile Leu Ser Ile Leu Arg His Gln Asn Leu Leu Lys Glu Leu Gln
65                  70                  75                  80

Asp Leu Ala Leu Gln Gly Ala Lys Glu Arg Ala His Gln Gln Lys Lys
                85                  90                  95

His Ser Gly Phe Glu Asp Glu Leu Ser Glu Val Leu Glu Asn Gln Ser
            100                 105                 110

Ser Gln Ala Glu Leu Lys Glu Ala Val Glu Glu Pro Ser Ser Lys Asp
            115                 120                 125

Val Met Glu Lys Arg Glu Asp Ser Lys Glu Ala Glu Lys Ser Gly Glu
            130                 135                 140

Ala Thr Asp Gly Ala Arg Pro Gln Ala Leu Pro Glu Pro Met Gln Glu
145                 150                 155                 160

Ser Lys Ala Glu Gly Asn Asn Gln Ala Pro Gly Glu Glu Glu Glu Glu
                165                 170                 175

Glu Glu Glu Ala Thr Asn Thr His Pro Pro Ala Ser Leu Pro Ser Gln
            180                 185                 190

Lys Tyr Pro Gly Pro Gln Ala Glu Gly Asp Ser Glu Gly Leu Ser Gln
            195                 200                 205

Gly Leu Val Asp Arg Glu Lys Gly Leu Ser Ala Glu Pro Gly Trp Gln
        210                 215                 220

Ala Lys Arg Glu Glu Glu Glu Glu Glu Glu Glu Glu Ala Glu Ala Gly
```

```
              225                 230                 235                 240
Glu Glu Ala Val Pro Glu Glu Gly Pro Thr Val Val Leu Asn Pro
                245                 250                 255

His Pro Ser Leu Gly Tyr Lys Glu Ile Arg Lys Gly Glu Ser Arg Ser
            260                 265                 270

Glu Ala Leu Ala Val Asp Gly Ala Lys Pro Gly Ala Glu Glu Ala
            275                 280                 285

Gln Asp Pro Glu Gly Lys Gly Glu Gln Glu His Ser Gln Gln Lys Glu
            290                 295                 300

Glu Glu Glu Glu Met Ala Val Val Pro Gln Gly Leu Phe Arg Gly Gly
305                 310                 315                 320

Lys Ser Gly Glu Leu Glu Gln Glu Glu Glu Arg Leu Ser Lys Glu Trp
                325                 330                 335

Glu Asp Ser Lys Arg Trp Ser Lys Met Asp Gln Leu Ala Lys Glu Leu
            340                 345                 350

Thr Ala Glu Lys Arg Leu Glu Gly Gln Glu Glu Glu Glu Asp Asn Arg
            355                 360                 365

Asp Ser Ser Met Lys Leu Ser Phe Arg Ala Arg Ala Tyr Gly Phe Arg
    370                 375                 380

Gly Pro Gly Pro Gln Leu Arg Arg Gly Trp Arg Pro Ser Ser Trp Glu
385                 390                 395                 400

Asp Ser Leu Glu Ala Gly Leu Pro Leu Gln Val Arg Gly Tyr Pro Glu
                405                 410                 415

Glu Lys Lys Glu Glu Glu Gly Ser Ala Asn Arg Arg Pro Glu Asp Gln
            420                 425                 430

Glu Leu Glu Ser Leu Ser Ala Ile Glu Ala Glu Leu Glu Lys Val Ala
            435                 440                 445

His Gln Leu Gln Ala Leu Arg Arg Gly
    450                 455

<210> SEQ ID NO 6
<211> LENGTH: 224
<212> TYPE: PRT
<213> ORGANISM: Homo sapiens

<400> SEQUENCE: 6

Met Glu Lys Leu Leu Cys Phe Leu Val Leu Thr Ser Leu Ser His Ala
1               5                  10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
50                  55                  60

Arg Gly Thr Val Phe Ser Arg Met Pro Pro Arg Asp Lys Thr Met Arg
65                  70                  75                  80

Phe Phe Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
```

```
                145                 150                 155                 160
Gly Gly Asn Phe Glu Gly Ser Gln Ser Leu Val Gly Asp Ile Gly Asn
                    165                 170                 175

Val Asn Met Trp Asp Phe Val Leu Ser Pro Asp Glu Ile Asn Thr Ile
                180                 185                 190

Tyr Leu Gly Gly Pro Phe Ser Pro Asn Val Leu Asn Trp Arg Ala Leu
            195                 200                 205

Lys Tyr Glu Val Gln Gly Glu Val Phe Thr Lys Pro Gln Leu Trp Pro
        210                 215                 220

<210> SEQ ID NO 7
<211> LENGTH: 245
<212> TYPE: PRT
<213> ORGANISM: Homo sapiens

<400> SEQUENCE: 7

Met Thr Leu Phe Pro Val Leu Leu Phe Leu Val Ala Gly Leu Leu Pro
1               5                   10                  15

Ser Phe Pro Ala Asn Glu Asp Lys Asp Pro Ala Phe Thr Ala Leu Leu
                20                  25                  30

Thr Thr Gln Thr Gln Val Gln Arg Glu Ile Val Asn Lys His Asn Glu
            35                  40                  45

Leu Arg Arg Ala Val Ser Pro Pro Ala Arg Asn Met Leu Lys Met Glu
        50                  55                  60

Trp Asn Lys Glu Ala Ala Ala Asn Ala Gln Lys Trp Ala Asn Gln Cys
65                  70                  75                  80

Asn Tyr Arg His Ser Asn Pro Lys Asp Arg Met Thr Ser Leu Lys Cys
                85                  90                  95

Gly Glu Asn Leu Tyr Met Ser Ser Ala Ser Ser Ser Trp Ser Gln Ala
            100                 105                 110

Ile Gln Ser Trp Phe Asp Glu Tyr Asn Asp Phe Asp Phe Gly Val Gly
        115                 120                 125

Pro Lys Thr Pro Asn Ala Val Val Gly His Tyr Thr Gln Val Val Trp
    130                 135                 140

Tyr Ser Ser Tyr Leu Val Gly Cys Gly Asn Ala Tyr Cys Pro Asn Gln
145                 150                 155                 160

Lys Val Leu Lys Tyr Tyr Val Cys Gln Tyr Cys Pro Ala Gly Asn
                165                 170                 175

Trp Ala Asn Arg Leu Tyr Val Pro Tyr Glu Gln Gly Ala Pro Cys Ala
                180                 185                 190

Ser Cys Pro Asp Asn Cys Asp Asp Gly Leu Cys Thr Asn Gly Cys Lys
            195                 200                 205

Tyr Glu Asp Leu Tyr Ser Asn Cys Lys Ser Leu Lys Leu Thr Leu Thr
        210                 215                 220

Cys Lys His Gln Leu Val Arg Asp Ser Cys Lys Ala Ser Cys Asn Cys
225                 230                 235                 240

Ser Asn Ser Ile Tyr
                245

<210> SEQ ID NO 8
<211> LENGTH: 268
<212> TYPE: PRT
<213> ORGANISM: Homo sapiens

<400> SEQUENCE: 8

Met Lys Gln Ile Leu His Pro Ala Leu Glu Thr Thr Asp Pro Cys Ser
1               5                   10                  15
```

Thr Gly Phe Val Phe Pro Ala Met Thr Leu Phe Pro Val Leu Leu Phe
            20                  25                  30

Leu Val Ala Gly Leu Leu Pro Ser Phe Pro Ala Asn Glu Asp Lys Asp
        35                  40                  45

Pro Ala Phe Thr Ala Leu Leu Thr Thr Gln Thr Gln Val Gln Arg Glu
    50                  55                  60

Ile Val Asn Lys His Asn Glu Leu Arg Arg Ala Val Ser Pro Pro Ala
65                  70                  75                  80

Arg Asn Met Leu Lys Met Glu Trp Asn Lys Glu Ala Ala Asn Ala
                85                  90                  95

Gln Lys Trp Ala Asn Gln Cys Asn Tyr Arg His Ser Asn Pro Lys Asp
            100                 105                 110

Arg Met Thr Ser Leu Lys Cys Gly Glu Asn Leu Tyr Met Ser Ser Ala
            115                 120                 125

Ser Ser Ser Trp Ser Gln Ala Ile Gln Ser Trp Phe Asp Glu Tyr Asn
130                 135                 140

Asp Phe Asp Phe Gly Val Gly Pro Lys Thr Pro Asn Ala Val Val Gly
145                 150                 155                 160

His Tyr Thr Gln Val Val Trp Tyr Ser Ser Tyr Leu Val Gly Cys Gly
            165                 170                 175

Asn Ala Tyr Cys Pro Asn Gln Lys Val Leu Lys Tyr Tyr Val Cys
            180                 185                 190

Gln Tyr Cys Pro Ala Gly Asn Trp Ala Asn Arg Leu Tyr Val Pro Tyr
        195                 200                 205

Glu Gln Gly Ala Pro Cys Ala Ser Cys Pro Asp Asn Cys Asp Asp Gly
    210                 215                 220

Leu Cys Thr Asn Gly Cys Lys Tyr Glu Asp Leu Tyr Ser Asn Cys Lys
225                 230                 235                 240

Ser Leu Lys Leu Thr Leu Thr Cys Lys His Gln Leu Val Arg Asp Ser
                245                 250                 255

Cys Lys Ala Ser Cys Asn Cys Ser Asn Ser Ile Tyr
            260                 265

<210> SEQ ID NO 9
<211> LENGTH: 258
<212> TYPE: PRT
<213> ORGANISM: Homo sapiens

<400> SEQUENCE: 9

Met Lys Gln Ile Leu His Pro Ala Leu Glu Thr Thr Ala Met Thr Leu
 1                5                  10                  15

Phe Pro Val Leu Leu Phe Leu Val Ala Gly Leu Leu Pro Ser Phe Pro
            20                  25                  30

Ala Asn Glu Asp Lys Asp Pro Ala Phe Thr Ala Leu Leu Thr Thr Gln
        35                  40                  45

Thr Gln Val Gln Arg Glu Ile Val Asn Lys His Asn Glu Leu Arg Arg
    50                  55                  60

Ala Val Ser Pro Pro Ala Arg Asn Met Leu Lys Met Glu Trp Asn Lys
65                  70                  75                  80

Glu Ala Ala Ala Asn Ala Gln Lys Trp Ala Asn Gln Cys Asn Tyr Arg
                85                  90                  95

His Ser Asn Pro Lys Asp Arg Met Thr Ser Leu Lys Cys Gly Glu Asn
            100                 105                 110

Leu Tyr Met Ser Ser Ala Ser Ser Ser Trp Ser Gln Ala Ile Gln Ser
            115                 120                 125

```
Trp Phe Asp Glu Tyr Asn Asp Phe Asp Phe Gly Val Gly Pro Lys Thr
        130                 135                 140

Pro Asn Ala Val Val Gly His Tyr Thr Gln Val Val Trp Tyr Ser Ser
145                 150                 155                 160

Tyr Leu Val Gly Cys Gly Asn Ala Tyr Cys Pro Asn Gln Lys Val Leu
                165                 170                 175

Lys Tyr Tyr Tyr Val Cys Gln Tyr Cys Pro Ala Gly Asn Trp Ala Asn
            180                 185                 190

Arg Leu Tyr Val Pro Tyr Glu Gln Gly Ala Pro Cys Ala Ser Cys Pro
        195                 200                 205

Asp Asn Cys Asp Asp Gly Leu Cys Thr Asn Gly Cys Lys Tyr Glu Asp
    210                 215                 220

Leu Tyr Ser Asn Cys Lys Ser Leu Lys Leu Thr Leu Thr Cys Lys His
225                 230                 235                 240

Gln Leu Val Arg Asp Ser Cys Lys Ala Ser Cys Asn Cys Ser Asn Ser
                245                 250                 255

Ile Tyr

<210> SEQ ID NO 10
<211> LENGTH: 486
<212> TYPE: PRT
<213> ORGANISM: Homo sapiens

<400> SEQUENCE: 10

Met Ile Gln Thr Val Pro Asp Pro Ala Ala His Ile Lys Glu Ala Leu
  1               5                  10                  15

Ser Val Val Ser Glu Asp Gln Ser Leu Phe Glu Cys Ala Tyr Gly Thr
                20                  25                  30

Pro His Leu Ala Lys Thr Glu Met Thr Ala Ser Ser Ser Ser Asp Tyr
            35                  40                  45

Gly Gln Thr Ser Lys Met Ser Pro Arg Val Pro Gln Gln Asp Trp Leu
        50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
    210                 215                 220

Leu Met His Ala Arg Asn Thr Gly Gly Ala Ala Phe Ile Phe Pro Asn
225                 230                 235                 240
```

-continued

```
Thr Ser Val Tyr Pro Glu Ala Thr Gln Arg Ile Thr Thr Arg Pro Asp
            245                 250                 255

Leu Pro Tyr Glu Pro Pro Arg Arg Ser Ala Trp Thr Gly His Gly His
            260                 265                 270

Pro Thr Pro Gln Ser Lys Ala Ala Gln Pro Ser Pro Ser Thr Val Pro
            275                 280                 285

Lys Thr Glu Asp Gln Arg Pro Gln Leu Asp Pro Tyr Gln Ile Leu Gly
            290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Asn Ser Ser Cys
            325                 330                 335

Ile Thr Trp Glu Gly Thr Asn Gly Glu Phe Lys Met Thr Asp Pro Asp
            340                 345                 350

Glu Val Ala Arg Arg Trp Gly Glu Arg Lys Ser Lys Pro Asn Met Asn
            355                 360                 365

Tyr Asp Lys Leu Ser Arg Ala Leu Arg Tyr Tyr Asp Lys Asn Ile
            370                 375                 380

Met Thr Lys Val His Gly Lys Arg Tyr Ala Tyr Lys Phe Asp Phe His
385                 390                 395                 400

Gly Ile Ala Gln Ala Leu Gln Pro His Pro Pro Glu Ser Ser Leu Tyr
            405                 410                 415

Lys Tyr Pro Ser Asp Leu Pro Tyr Met Gly Ser Tyr His Ala His Pro
            420                 425                 430

Gln Lys Met Asn Phe Val Ala Pro His Pro Pro Ala Leu Pro Val Thr
            435                 440                 445

Ser Ser Ser Phe Phe Ala Ala Pro Asn Pro Tyr Trp Asn Ser Pro Thr
450                 455                 460

Gly Gly Ile Tyr Pro Asn Thr Arg Leu Pro Thr Ser His Met Pro Ser
465                 470                 475                 480

His Leu Gly Thr Tyr Tyr
                485
```

<210> SEQ ID NO 11
<211> LENGTH: 317
<212> TYPE: PRT
<213> ORGANISM: Homo sapiens

<400> SEQUENCE: 11

```
Met Ile Gln Thr Val Pro Asp Pro Ala Ala His Ile Lys Glu Ala Leu
 1               5                  10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
            35                  40                  45

Gly Gln Thr Ser Lys Met Ser Pro Arg Val Pro Gln Gln Asp Trp Leu
            50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
            85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Pro Asn Met Thr Thr Asn
            115                 120                 125
```

```
Glu Arg Arg Val Ile Val Pro Ala Asp Pro Thr Leu Trp Ser Thr Asp
        130                 135                 140
His Val Arg Gln Trp Leu Glu Trp Ala Val Lys Glu Tyr Gly Leu Pro
145                 150                 155                 160
Asp Val Asn Ile Leu Leu Phe Gln Asn Ile Asp Gly Lys Glu Leu Cys
                165                 170                 175
Lys Met Thr Lys Asp Asp Phe Gln Arg Leu Thr Pro Ser Tyr Asn Ala
                180                 185                 190
Asp Ile Leu Leu Ser His Leu His Tyr Leu Arg Glu Thr Pro Leu Pro
                195                 200                 205
His Leu Thr Ser Asp Asp Val Asp Lys Ala Leu Gln Asn Ser Pro Arg
        210                 215                 220
Leu Met His Ala Arg Asn Thr Gly Gly Ala Ala Phe Ile Phe Pro Asn
225                 230                 235                 240
Thr Ser Val Tyr Pro Glu Ala Thr Gln Arg Ile Thr Thr Arg Pro Asp
                245                 250                 255
Leu Pro Tyr Glu Pro Pro Arg Arg Ser Ala Trp Thr Gly His Gly His
                260                 265                 270
Pro Thr Pro Gln Ser Lys Ala Ala Gln Pro Ser Pro Ser Thr Val Pro
        275                 280                 285
Lys Thr Glu Asp Gln Arg Pro Gln Leu Asp Pro Tyr Gln Ile Leu Gly
        290                 295                 300
Pro Thr Ser Ser Arg Leu Ala Asn Pro Gly Trp Thr Gln
305                 310                 315
```

<210> SEQ ID NO 12
<211> LENGTH: 363
<212> TYPE: PRT
<213> ORGANISM: Homo sapiens

<400> SEQUENCE: 12

```
Met Val Gly Ser Pro Asp Thr Val Gly Met Asn Tyr Gly Ser Tyr Met
  1               5                  10                  15
Glu Glu Lys His Met Pro Pro Asn Met Thr Thr Asn Glu Arg Arg
                20                  25                  30
Val Ile Val Pro Ala Asp Pro Thr Leu Trp Ser Thr Asp His Val Arg
                35                  40                  45
Gln Trp Leu Glu Trp Ala Val Lys Glu Tyr Gly Leu Pro Asp Val Asn
        50                  55                  60
Ile Leu Leu Phe Gln Asn Ile Asp Gly Lys Glu Leu Cys Lys Met Thr
65                  70                  75                  80
Lys Asp Asp Phe Gln Arg Leu Thr Pro Ser Tyr Asn Ala Asp Ile Leu
                85                  90                  95
Leu Ser His Leu His Tyr Leu Arg Glu Thr Pro Leu Pro His Leu Thr
                100                 105                 110
Ser Asp Asp Val Asp Lys Ala Leu Gln Asn Ser Pro Arg Leu Met His
        115                 120                 125
Ala Arg Asn Thr Asp Leu Pro Tyr Glu Pro Pro Arg Arg Ser Ala Trp
        130                 135                 140
Thr Gly His Gly His Pro Thr Pro Gln Ser Lys Ala Ala Gln Pro Ser
145                 150                 155                 160
Pro Ser Thr Val Pro Lys Thr Glu Asp Gln Arg Pro Gln Leu Asp Pro
                165                 170                 175
Tyr Gln Ile Leu Gly Pro Thr Ser Ser Arg Leu Ala Asn Pro Gly Ser
                180                 185                 190
```

-continued

Gly Gln Ile Gln Leu Trp Gln Phe Leu Leu Glu Leu Leu Ser Asp Ser
            195                 200                 205

Ser Asn Ser Ser Cys Ile Thr Trp Glu Gly Thr Asn Gly Glu Phe Lys
210                 215                 220

Met Thr Asp Pro Asp Glu Val Ala Arg Arg Trp Gly Glu Arg Lys Ser
225                 230                 235                 240

Lys Pro Asn Met Asn Tyr Asp Lys Leu Ser Arg Ala Leu Arg Tyr Tyr
                245                 250                 255

Tyr Asp Lys Asn Ile Met Thr Lys Val His Gly Lys Arg Tyr Ala Tyr
            260                 265                 270

Lys Phe Asp Phe His Gly Ile Ala Gln Ala Leu Gln Pro His Pro Pro
        275                 280                 285

Glu Ser Ser Leu Tyr Lys Tyr Pro Ser Asp Leu Pro Tyr Met Gly Ser
290                 295                 300

Tyr His Ala His Pro Gln Lys Met Asn Phe Val Ala Pro His Pro Pro
305                 310                 315                 320

Ala Leu Pro Val Thr Ser Ser Phe Phe Ala Ala Pro Asn Pro Tyr
                325                 330                 335

Trp Asn Ser Pro Thr Gly Gly Ile Tyr Pro Asn Thr Arg Leu Pro Thr
            340                 345                 350

Ser His Met Pro Ser His Leu Gly Thr Tyr Tyr
        355                 360

<210> SEQ ID NO 13
<211> LENGTH: 387
<212> TYPE: PRT
<213> ORGANISM: Homo sapiens

<400> SEQUENCE: 13

Met Val Gly Ser Pro Asp Thr Val Gly Met Asn Tyr Gly Ser Tyr Met
1               5                   10                  15

Glu Glu Lys His Met Pro Pro Pro Asn Met Thr Thr Asn Glu Arg Arg
            20                  25                  30

Val Ile Val Pro Ala Asp Pro Thr Leu Trp Ser Thr Asp His Val Arg
        35                  40                  45

Gln Trp Leu Glu Trp Ala Val Lys Glu Tyr Gly Leu Pro Asp Val Asn
    50                  55                  60

Ile Leu Leu Phe Gln Asn Ile Asp Gly Lys Glu Leu Cys Lys Met Thr
65                  70                  75                  80

Lys Asp Asp Phe Gln Arg Leu Thr Pro Ser Tyr Asn Ala Asp Ile Leu
                85                  90                  95

Leu Ser His Leu His Tyr Leu Arg Glu Thr Pro Leu Pro His Leu Thr
            100                 105                 110

Ser Asp Asp Val Asp Lys Ala Leu Gln Asn Ser Pro Arg Leu Met His
        115                 120                 125

Ala Arg Asn Thr Gly Gly Ala Ala Phe Ile Phe Pro Asn Thr Ser Val
    130                 135                 140

Tyr Pro Glu Ala Thr Gln Arg Ile Thr Thr Arg Pro Asp Leu Pro Tyr
145                 150                 155                 160

Glu Pro Pro Arg Arg Ser Ala Trp Thr Gly His Gly His Pro Thr Pro
                165                 170                 175

Gln Ser Lys Ala Ala Gln Pro Ser Pro Ser Thr Val Pro Lys Thr Glu
            180                 185                 190

Asp Gln Arg Pro Gln Leu Asp Pro Tyr Gln Ile Leu Gly Pro Thr Ser
        195                 200                 205

-continued

Ser Arg Leu Ala Asn Pro Gly Ser Gly Gln Ile Gln Leu Trp Gln Phe
    210                 215                 220

Leu Leu Glu Leu Leu Ser Asp Ser Ser Asn Ser Ser Cys Ile Thr Trp
225                 230                 235                 240

Glu Gly Thr Asn Gly Glu Phe Lys Met Thr Asp Pro Asp Glu Val Ala
                245                 250                 255

Arg Arg Trp Gly Glu Arg Lys Ser Lys Pro Asn Met Asn Tyr Asp Lys
            260                 265                 270

Leu Ser Arg Ala Leu Arg Tyr Tyr Tyr Asp Lys Asn Ile Met Thr Lys
        275                 280                 285

Val His Gly Lys Arg Tyr Ala Tyr Lys Phe Asp Phe His Gly Ile Ala
    290                 295                 300

Gln Ala Leu Gln Pro His Pro Pro Glu Ser Ser Leu Tyr Lys Tyr Pro
305                 310                 315                 320

Ser Asp Leu Pro Tyr Met Gly Ser Tyr His Ala His Pro Gln Lys Met
                325                 330                 335

Asn Phe Val Ala Pro His Pro Pro Ala Leu Pro Val Thr Ser Ser Ser
            340                 345                 350

Phe Phe Ala Ala Pro Asn Pro Tyr Trp Asn Ser Pro Thr Gly Gly Ile
        355                 360                 365

Tyr Pro Asn Thr Arg Leu Pro Thr Ser His Met Pro Ser His Leu Gly
    370                 375                 380

Thr Tyr Tyr
385

<210> SEQ ID NO 14
<211> LENGTH: 486
<212> TYPE: PRT
<213> ORGANISM: Homo sapiens

<400> SEQUENCE: 14

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
    210                 215                 220

Leu Met His Ala Arg Asn Thr Gly Gly Ala Ala Phe Ile Phe Pro Asn
225                 230                 235                 240

Thr Ser Val Tyr Pro Glu Ala Thr Gln Arg Ile Thr Thr Arg Pro Asp
                245                 250                 255

Leu Pro Tyr Glu Pro Pro Arg Arg Ser Ala Trp Thr Gly His Gly His
            260                 265                 270

Pro Thr Pro Gln Ser Lys Ala Ala Gln Pro Ser Pro Thr Val Pro
                275                 280                 285

Lys Thr Glu Asp Gln Arg Pro Gln Leu Asp Pro Tyr Gln Ile Leu Gly
    290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Ser Asn Ser Ser Cys
                325                 330                 335

Ile Thr Trp Glu Gly Thr Asn Gly Glu Phe Lys Met Thr Asp Pro Asp
                340                 345                 350

Glu Val Ala Arg Arg Trp Gly Glu Arg Lys Ser Lys Pro Asn Met Asn
                355                 360                 365

Tyr Asp Lys Leu Ser Arg Ala Leu Arg Tyr Tyr Asp Lys Asn Ile
    370                 375                 380

Met Thr Lys Val His Gly Lys Arg Tyr Ala Tyr Lys Phe Asp Phe His
385                 390                 395                 400

Gly Ile Ala Gln Ala Leu Gln Pro His Pro Glu Ser Ser Leu Tyr
                405                 410                 415

Lys Tyr Pro Ser Asp Leu Pro Tyr Met Gly Ser Tyr His Ala His Pro
                420                 425                 430

Gln Lys Met Asn Phe Val Ala Pro His Pro Ala Leu Pro Val Thr
    435                 440                 445

Ser Ser Ser Phe Phe Ala Ala Pro Asn Pro Tyr Trp Asn Ser Pro Thr
    450                 455                 460

Gly Gly Ile Tyr Pro Asn Thr Arg Leu Pro Thr Ser His Met Pro Ser
465                 470                 475                 480

His Leu Gly Thr Tyr Tyr
                485

<210> SEQ ID NO 15
<211> LENGTH: 462
<212> TYPE: PRT
<213> ORGANISM: Homo sapiens

<400> SEQUENCE: 15

Met Ile Gln Thr Val Pro Asp Pro Ala Ala His Ile Lys Glu Ala Leu
  1               5                  10                  15

Ser Val Val Ser Glu Asp Gln Ser Leu Phe Glu Cys Ala Tyr Gly Thr
                 20                  25                  30

Pro His Leu Ala Lys Thr Glu Met Thr Ala Ser Ser Ser Ser Asp Tyr
             35                  40                  45

Gly Gln Thr Ser Lys Met Ser Pro Arg Val Pro Gln Gln Asp Trp Leu
         50                  55                  60

Ser Gln Pro Pro Ala Arg Val Thr Ile Lys Met Glu Cys Asn Pro Ser
 65                  70                  75                  80

```
Gln Val Asn Gly Ser Arg Asn Ser Pro Asp Glu Cys Ser Val Ala Lys
                 85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
    210                 215                 220

Leu Met His Ala Arg Asn Thr Asp Leu Pro Tyr Glu Pro Pro Arg Arg
225                 230                 235                 240

Ser Ala Trp Thr Gly His Gly His Pro Thr Pro Gln Ser Lys Ala Ala
                245                 250                 255

Gln Pro Ser Pro Ser Thr Val Pro Lys Thr Glu Asp Gln Arg Pro Gln
            260                 265                 270

Leu Asp Pro Tyr Gln Ile Leu Gly Pro Thr Ser Ser Arg Leu Ala Asn
        275                 280                 285

Pro Gly Ser Gly Gln Ile Gln Leu Trp Gln Phe Leu Leu Glu Leu Leu
    290                 295                 300

Ser Asp Ser Ser Asn Ser Ser Cys Ile Thr Trp Glu Gly Thr Asn Gly
305                 310                 315                 320

Glu Phe Lys Met Thr Asp Pro Asp Glu Val Ala Arg Arg Trp Gly Glu
                325                 330                 335

Arg Lys Ser Lys Pro Asn Met Asn Tyr Asp Lys Leu Ser Arg Ala Leu
            340                 345                 350

Arg Tyr Tyr Tyr Asp Lys Asn Ile Met Thr Lys Val His Gly Lys Arg
        355                 360                 365

Tyr Ala Tyr Lys Phe Asp Phe His Gly Ile Ala Gln Ala Leu Gln Pro
    370                 375                 380

His Pro Pro Glu Ser Ser Leu Tyr Lys Tyr Pro Ser Asp Leu Pro Tyr
385                 390                 395                 400

Met Gly Ser Tyr His Ala His Pro Gln Lys Met Asn Phe Val Ala Pro
                405                 410                 415

His Pro Pro Ala Leu Pro Val Thr Ser Ser Ser Phe Phe Ala Ala Pro
            420                 425                 430

Asn Pro Tyr Trp Asn Ser Pro Thr Gly Gly Ile Tyr Pro Asn Thr Arg
        435                 440                 445

Leu Pro Thr Ser His Met Pro Ser His Leu Gly Thr Tyr Tyr
    450                 455                 460

<210> SEQ ID NO 16
<211> LENGTH: 479
<212> TYPE: PRT
<213> ORGANISM: Homo sapiens

<400> SEQUENCE: 16
```

```
Met Ala Ser Thr Ile Lys Glu Ala Leu Ser Val Val Ser Glu Asp Gln
 1               5                  10                  15
Ser Leu Phe Glu Cys Ala Tyr Gly Thr Pro His Leu Ala Lys Thr Glu
             20                  25                  30
Met Thr Ala Ser Ser Ser Asp Tyr Gly Gln Thr Ser Lys Met Ser
         35                  40                  45
Pro Arg Val Pro Gln Gln Asp Trp Leu Ser Gln Pro Ala Arg Val
 50                  55                  60
Thr Ile Lys Met Glu Cys Asn Pro Ser Gln Val Asn Gly Ser Arg Asn
 65                  70                  75                  80
Ser Pro Asp Glu Cys Ser Val Ala Lys Gly Lys Met Val Gly Ser
                 85                  90                  95
Pro Asp Thr Val Gly Met Asn Tyr Gly Ser Tyr Met Glu Glu Lys His
             100                 105                 110
Met Pro Pro Pro Asn Met Thr Thr Asn Glu Arg Arg Val Ile Val Pro
             115                 120                 125
Ala Asp Pro Thr Leu Trp Ser Thr Asp His Val Arg Gln Trp Leu Glu
 130                 135                 140
Trp Ala Val Lys Glu Tyr Gly Leu Pro Asp Val Asn Ile Leu Leu Phe
145                 150                 155                 160
Gln Asn Ile Asp Gly Lys Glu Leu Cys Lys Met Thr Lys Asp Phe
                 165                 170                 175
Gln Arg Leu Thr Pro Ser Tyr Asn Ala Asp Ile Leu Leu Ser His Leu
             180                 185                 190
His Tyr Leu Arg Glu Thr Pro Leu Pro His Leu Thr Ser Asp Asp Val
             195                 200                 205
Asp Lys Ala Leu Gln Asn Ser Pro Arg Leu Met His Ala Arg Asn Thr
 210                 215                 220
Gly Gly Ala Ala Phe Ile Phe Pro Asn Thr Ser Val Tyr Pro Glu Ala
225                 230                 235                 240
Thr Gln Arg Ile Thr Thr Arg Pro Asp Leu Pro Tyr Glu Pro Pro Arg
                 245                 250                 255
Arg Ser Ala Trp Thr Gly His Gly His Pro Thr Pro Gln Ser Lys Ala
             260                 265                 270
Ala Gln Pro Ser Pro Ser Thr Val Pro Lys Thr Glu Asp Gln Arg Pro
             275                 280                 285
Gln Leu Asp Pro Tyr Gln Ile Leu Gly Pro Thr Ser Ser Arg Leu Ala
 290                 295                 300
Asn Pro Gly Ser Gly Gln Ile Gln Leu Trp Gln Phe Leu Leu Glu Leu
305                 310                 315                 320
Leu Ser Asp Ser Asn Ser Ser Cys Ile Thr Trp Glu Gly Thr Asn
                 325                 330                 335
Gly Glu Phe Lys Met Thr Asp Pro Asp Glu Val Ala Arg Arg Trp Gly
             340                 345                 350
Glu Arg Lys Ser Lys Pro Asn Met Asn Tyr Asp Lys Leu Ser Arg Ala
             355                 360                 365
Leu Arg Tyr Tyr Tyr Asp Lys Asn Ile Met Thr Lys Val His Gly Lys
 370                 375                 380
Arg Tyr Ala Tyr Lys Phe Asp Phe His Gly Ile Ala Gln Ala Leu Gln
385                 390                 395                 400
Pro His Pro Pro Glu Ser Ser Leu Tyr Lys Tyr Pro Ser Asp Leu Pro
                 405                 410                 415
Tyr Met Gly Ser Tyr His Ala His Pro Gln Lys Met Asn Phe Val Ala
             420                 425                 430
```

```
Pro His Pro Pro Ala Leu Pro Val Thr Ser Ser Ser Phe Phe Ala Ala
        435                 440                 445

Pro Asn Pro Tyr Trp Asn Ser Pro Thr Gly Gly Ile Tyr Pro Asn Thr
    450                 455                 460

Arg Leu Pro Thr Ser His Met Pro Ser His Leu Gly Thr Tyr Tyr
465                 470                 475

<210> SEQ ID NO 17
<211> LENGTH: 524
<212> TYPE: PRT
<213> ORGANISM: Homo sapiens

<400> SEQUENCE: 17

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335
```

```
Asp His Gly His His Glu Gly Lys Ala Lys Gln Ala Leu His Glu Ala
            340                 345                 350
Val Glu Met Asp Arg Ala Ile Gly Gln Ala Gly Ser Leu Thr Ser Ser
        355                 360                 365
Glu Asp Thr Leu Thr Val Val Thr Ala Asp His Ser His Val Phe Thr
370                 375                 380
Phe Gly Gly Tyr Thr Pro Arg Gly Asn Ser Ile Phe Gly Leu Ala Pro
385                 390                 395                 400
Met Leu Ser Asp Thr Asp Lys Lys Pro Phe Thr Ala Ile Leu Tyr Gly
                405                 410                 415
Asn Gly Pro Gly Tyr Lys Val Val Gly Glu Arg Glu Asn Val Ser
            420                 425                 430
Met Val Asp Tyr Ala His Asn Asn Tyr Gln Ala Gln Ser Ala Val Pro
        435                 440                 445
Leu Arg His Glu Thr His Gly Gly Glu Asp Val Ala Val Phe Ser Lys
450                 455                 460
Gly Pro Met Ala His Leu Leu His Gly Val His Glu Gln Asn Tyr Val
465                 470                 475                 480
Pro His Val Met Ala Tyr Ala Ala Cys Ile Gly Ala Asn Leu Gly His
                485                 490                 495
Cys Ala Pro Ala Ser Ser Ala Gly Ser Leu Ala Gly Pro Leu Leu
            500                 505                 510
Leu Ala Leu Ala Leu Tyr Pro Leu Ser Val Leu Phe
            515                 520

<210> SEQ ID NO 18
<211> LENGTH: 261
<212> TYPE: PRT
<213> ORGANISM: Homo sapiens

<400> SEQUENCE: 5

Met Trp Asp Leu Val Leu Ser Ile Ala Leu Ser Val Gly Cys Thr Gly
1               5                   10                  15
Ala Val Pro Leu Ile Gln Ser Arg Ile Val Gly Gly Trp Glu Cys Glu
            20                  25                  30
Lys His Ser Gln Pro Trp Gln Val Ala Val Tyr Ser His Gly Trp Ala
        35                  40                  45
His Cys Gly Gly Val Leu Val His Pro Gln Trp Val Leu Thr Ala Ala
    50                  55                  60
His Cys Leu Lys Lys Asn Ser Gln Val Trp Leu Gly Arg His Asn Leu
65                  70                  75                  80
Phe Glu Pro Glu Asp Thr Gly Gln Arg Val Pro Val Ser His Ser Phe
                85                  90                  95
Pro His Pro Leu Tyr Asn Met Ser Leu Leu Lys His Gln Ser Leu Arg
            100                 105                 110
Pro Asp Glu Asp Ser Ser His Asp Leu Met Leu Leu Arg Leu Ser Glu
        115                 120                 125
Pro Ala Lys Ile Thr Asp Val Val Lys Val Leu Gly Leu Pro Thr Gln
    130                 135                 140
Glu Pro Ala Leu Gly Thr Thr Cys Tyr Ala Ser Gly Trp Gly Ser Ile
145                 150                 155                 160
Glu Pro Glu Glu Phe Leu Arg Pro Arg Ser Leu Gln Cys Val Ser Leu
                165                 170                 175
His Leu Leu Ser Asn Asp Met Cys Ala Arg Ala Tyr Ser Glu Lys Val
            180                 185                 190
```

```
Thr Glu Phe Met Leu Cys Ala Gly Leu Trp Thr Gly Gly Lys Asp Thr
            195                 200                 205

Cys Gly Gly Asp Ser Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
            245                 250                 255

Ile Ala Ala Asn Pro
            260

<210> SEQ ID NO 19
<211> LENGTH: 223
<212> TYPE: PRT
<213> ORGANISM: Homo sapiens

<400> SEQUENCE: 6

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Val Ser His Pro Tyr Ser Gln His Leu Glu Gly Lys Gly
    210                 215                 220

<210> SEQ ID NO 20
<211> LENGTH: 386
<212> TYPE: PRT
<213> ORGANISM: Homo sapiens

<400> SEQUENCE: 9

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30
```

-continued

Lys Glu Leu Lys Phe Val Thr Leu Val Phe Arg His Gly Asp Arg Ser
            35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
            115                 120                 125

Val Ser Ile Trp Asn Pro Ile Leu Leu Trp Gln Pro Ile Pro Val His
            130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
            195                 200                 205

Val Tyr Asp Pro Leu Tyr Cys Glu Ser Val His Asn Phe Thr Leu Pro
210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
            275                 280                 285

His Asp Thr Thr Val Ser Gly Leu Gln Met Ala Leu Asp Val Tyr Asn
            290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
            355                 360                 365

Ser Thr Glu Cys Met Thr Thr Asn Ser His Gln Gly Thr Glu Asp Ser
370                 375                 380

Thr Asp
385

METHODS AND MATERIALS FOR DETERMINING THE EFFICACY OF PROSTATE CANCER THERAPIES

REFERENCE TO RELATED APPLICATIONS

This application is a continuation-in-part of U.S. patent application Ser. No. 13/291,994, filed Nov. 8, 2011, the disclosure of which is hereby incorporated by reference.

REFERENCE TO SEQUENCE LISTING

This application incorporates by reference in its entirety the Sequence Listing contained in the accompanying file, named "1005CIP_seqlist.txt," the size of which is 51 KB, and which was created on Aug. 22, 2012.

TECHNICAL FIELD

The present disclosure relates to methods and compositions for determining and monitoring the efficacy of therapeutic interventions employed in the treatment of prostate cancer.

BACKGROUND

In many countries prostate cancer is the most common, or the second most common, cancer diagnosed in males. Unless detected early, prostate cancer may spread to the spine and bones of the patient, causing severe pain, bone frailty and death. Between 20 and 30,000 men die each year in the United States, 600 in New Zealand and 2000 in Australia, from prostate cancer. The use of prostate specific antigen (PSA) as a diagnostic biomarker for prostate cancer was approved by the US Federal Drug Agency in 1994. In the nearly two decades since this approval, the PSA test has remained the primary tool for use in prostate cancer diagnosis, in monitoring for recurrence of prostate cancer, and in following the efficacy of treatments. However the PSA test has multiple shortcomings and, despite its widespread use, has resulted in only small changes in the death rate from advanced prostate cancers. To reduce the death rate and the negative impacts on quality of life caused by prostate cancer, new tools are required for more accurate primary diagnosis, for assessing the risk of spread of primary prostate cancers, and for monitoring responses to therapeutic interventions.

The PSA blood test is not used in isolation when checking for prostate cancer; a digital rectal examination (DRE) is usually also performed. If the results of the PSA test or the DRE are abnormal, a biopsy is generally performed in which small samples of tissue are removed from the prostate and examined. If the results are positive for prostate cancer, further tests may be needed to determine the stage of progression of the cancer, such as a bone scan, a computed tomography (CT) scan or a pelvic lymph node dissection.

Currently, the established prognostic factors of histological grade and cancer stage from biopsy results, and prostate-specific antigen level in blood at diagnosis are insufficient to separate prostate cancer patients who are at high risk for cancer progression and require aggressive treatment, from those who are likely to die of another cause.

An important clinical question is how aggressively to treat patients with localized prostate cancer. Treatment options for more aggressive cancers are invasive and include radical prostatectomy and/or radiation therapy. Androgen-depletion therapy, for example using gonadotropin-releasing hormone agonists (e.g., leuprolide, goserelin, etc.), is designed to reduce the amount of testosterone that enters the prostate gland and is used in patients with metastatic disease, some patients who have a rising PSA and choose not to have surgery or radiation, and some patients with a rising PSA after surgery or radiation. Treatment options usually depend on the stage of the prostate cancer. Men with a 10-year life expectancy or less, who have a low Gleason score from a biopsy and whose cancer has not spread beyond the prostate are often not treated. Younger men with a low Gleason score and a prostate-restricted cancer may enter a phase of "watchful waiting" in which treatment is withheld until signs of progression are identified. However, these prognostic indicators do not accurately predict clinical outcome for individual patients.

One feature of prostate cancer is that the phenotype of the disease varies from one patient to another. This is the major problem confronting the physician who seeks to develop the best treatment protocol for each patient. Prostate cancer in different individuals displays very heterogeneous cellular morphologies, growth rates, responsiveness to androgen and its pharmacological blocking agents, and metastatic potential. This heterogeneity in cancer phenotype is reflected in the treatment regimes used by physicians in that different prostate cancer phenotypes are responsive to very different drug regimes.

Treatment options for patients with metastatic prostate cancer are limited in their effectiveness. After development of resistance to androgen-depletion therapy, a patient may proceed to second-line hormonal therapy with ketoconazole, estrogen and Leukine™, and then to docetaxel chemotherapy (Tannock et al., N Engl J. Med. 2004; 351:1502-1512; de Bono et al., N Engl J Med. 2011; 364:1995-2005; de Bono et al., Lancet. 2010; 376:1147-1154; Kantoff et al., N Engl J Med. 2010; 363:411-422). After ketoconazole and docetaxel, the treatment options left for metastatic prostate cancer patients are three further drugs with FDA approval, namely Jevtana™ (cabazitaxel), Provenge™ (Sipuleucel-T) and Zytiga™ (abiraterone), but all are associated with median survivals of less than 2 years. In part, the impact on survival is the result of low response rates, indicating a significant proportion of patients exhibiting de novo resistance to these agents. Other drugs used in the treatment of other cancers, such as Sprycel™, show promise in use against prostate cancer. After the use of FDA-approved drugs, there is a fairly long list of drugs where phase II results suggest possible clinical utility against prostate cancer, including Novantrone™, 5-fluorouracil, doxorubicin, platinum-based drugs, methotrexate and etoposide. However, there is been no reliable way to identify which of these drugs might have the greatest chance at success in treating specific patients.

For each drug application, routine follow-up laboratory tests are used to monitor the health of the patient. These include haemoglobin levels, blood cell count, platelet count, creatinine levels, liver enzymes, alkaline phosphatase and bilirubin. Different patients respond differently to chemotherapy and response rates are low. This is due to the patient's phenotype as revealed by the spectrum of side-effects caused by differences in drug metabolism and pharmacokinetics, polymorphism of detoxification enzymes leading to drug toxicity, and a general suppression of innate and adaptive immunity.

For prostate cancer patients, a major issue is that the androgen receptor numbers in cells increase in many prostate cancers after chemotherapy (Culig et al., J Cell Biochem. 2006; 99:373-381). This is why new drugs, such as Zytiga™ and now Enzalutamide (MDV3100) have been developed to try and circumvent the role of the receptors. Some metastatic and primary prostate cancers retain activation of the androgen receptor in processes that are entirely independent of the androgen ligand. There are a number of mechanisms for this, including up-regulation of androgen receptor expression through amplification of the androgen receptor gene (Visakorpi et al., Nat Genet 1995; 9:401; Chen et al., Nat Med 2004; 10:33; Edwards et al., Br J Cancer 2003; 89:552), increased sensitivity of androgen receptor via overexpression of nuclear co-activators (Gregory et al., Cancer Res 2001; 61:2892.), and splice variant mutations of the receptor (Watson et al., Proc Natl Acad Sci USA 2010; 107:16759; Guo et al., Cancer Res 2009; 69:2305).

While there is a report of the molecular profiling of patients showing overexpression of the androgen receptor after a failed response to docetaxel, and then a dramatic response of measurable disease to second-line hormonal therapy with ketoconazole, estrogen and Leukine™ (Myers et al., Case Rep Oncol. 2012 January-April; 5(1): 154-158), little has been done to try and evaluate why patients fail chemotherapy.

There are currently no effective tests to monitor whether or not a patient is responding to a particular therapy, such as administration of one or more chemotherapeutic agents. The ability to monitor the effectiveness of an on-going treatment regime in a patient would enable a clinician to determine whether the patient should remain on that regime or should be put on a different treatment regime. There thus remains a need in the art for an accurate test for monitoring the efficacy of treatment regimes in subjects with prostate cancer.

SUMMARY

The present invention provides a minimally invasive test that can be employed to monitor the efficacy of treatment regimes in prostate cancer patients, together with materials for performing the test. The disclosed methods detect multiple biomarkers and correlate their expression levels with the progression or regression of prostate cancer in a subject. In certain embodiments, the methods utilize patterns of expression of biomarkers to distinguish between subjects who are responding to a particular prostate cancer treatment regime and those who are not responding to the regime.

In one embodiment, methods for determining the efficacy of a treatment for prostate cancer in a subject are provided, such methods comprising: (a) detecting levels of expression of a plurality of biomarkers in biological samples obtained from the subject at different time intervals prior to and following administration of the treatment, wherein the plurality of polypeptide biomarkers comprises prostate specific antigen (PSA) and at least one biomarker selected from the group consisting of: C reactive protein (CRP), chromogranin A (CHGA), bone alkaline phosphatase (BAP), cysteine-rich secretory protein 3 (CRISP3), ERG, and prostatic acid phosphatase (PAP; also called ACP3; human acid phosphatase 3, prostatic); and (b) determining changes in the levels of expression of the plurality of biomarkers following administration of the treatment, wherein a decrease in the level of expression of PSA and an increase in the level of expression of at least one biomarker selected from CRP, CHGA, BAP, CRISP3, PAP and ERG that is sustained for a period of at least one, two or more weeks indicates that the treatment is effective in treating prostate cancer in the subject. In certain embodiments, such methods comprise determining levels of expression of PSA plus at least two, three, four, five or six biomarkers selected from CRP, CHGA, BAP, CRISP3, ERG and PAP.

In another embodiment, the present disclosure provides methods for determining the efficacy of a treatment for prostate cancer in a subject, comprising: (a) detecting levels of expression of at least one biomarker in biological samples obtained from the subject at different time intervals prior to and following administration of the treatment, wherein the biomarker is selected from the group consisting of: C reactive protein (CRP), bone alkaline phosphatase (BAP) and cysteine-rich secretory protein 3 (CRISP3); and (b) determining changes in the level of expression of the at least one biomarker following administration of the treatment, wherein a rapid increase in the level of expression of the at least one biomarker that is sustained for a period of less than three or four weeks indicates that the treatment is not effective in treating prostate cancer in the subject. These increases may be extremely rapid, doubling in concentration (ng/ml) within, for example, two hours or more for a serum protein such as CRP, or two days or more for CRISP3. In certain embodiments, such methods comprise determining levels of expression of at least two or three biomarkers selected from CRP, BAP and CRISP3.

In a further embodiment, methods for determining the efficacy of a treatment for prostate cancer in a subject are provided that comprise: (a) detecting levels of expression of a plurality of biomarkers in biological samples obtained from the subject at different time intervals prior to and following administration of the treatment, wherein the plurality of polypeptide biomarkers comprises chromogranin A (CHGA), cysteine-rich secretory protein 3 (CRISP3), C reactive protein (CRP), prostatic acid phosphatase (PAP), ERG and bone alkaline phosphatase (BAP); and (b) determining changes in the levels of expression of the plurality of biomarkers following administration of the treatment, wherein an increase in the level of expression of at least one of the biomarkers of less than 5%, 10% or 15% indicates that the treatment is not effective in treating prostate cancer in the subject.

In yet another embodiment, the present disclosure provides methods for determining the efficacy of a treatment for prostate cancer in a subject that comprise: (a) detecting levels of expression of a plurality of biomarkers in biological samples obtained from the subject at different time intervals prior to and following administration of the treatment, wherein the plurality of polypeptide biomarkers comprises cysteine-rich secretory protein 3 (CRISP3) and ERG; and (b) determining changes in the levels of expression of the plurality of biomarkers following administration of the treatment, wherein an increase in expression of at least one of the biomarkers indicates that the treatment is effective in treating prostate cancer in the subject.

The polypeptide sequences for PSA, CRP, CHGA, BAP, CRISP3, ERG, PAP and KLK2 are provided in SEQ ID NO: 1-20. In certain embodiments, the methods disclosed herein include detecting the level of expression of a polypeptide comprising a sequence of SEQ ID NO: 1-20, or a variant thereof, as defined herein.

In certain embodiments, the methods disclosed herein are employed to monitor the efficacy of a treatment regime in a subject with metastatic prostate cancer. Biological samples that can be effectively employed in the disclosed methods include, but are not limited to, urine, blood and blood products (such as peripheral mononuclear cells (PBMCs)) and serum.

In certain embodiments, the expression levels of the polypeptide biomarkers employed herein are quantified by immunoassay, such as enzyme-linked immunoassay (ELISA) technology. In specific embodiments, the levels of expression of the polypeptide biomarkers are determined by contacting the biological sample with antibodies, or antigen binding fragments thereof, that selectively bind to the polypeptide biomarkers; and detecting binding of the antibodies, or antigen binding fragments thereof, to the polypeptide biomarkers. The binding agents employed in the disclosed methods and compositions are preferably labeled with a detectable moiety.

For example, the level of a polypeptide biomarker in a sample can be assayed by contacting the biological sample with an antibody, or antigen binding fragment thereof, that selectively binds to the target biomarker (referred to as a capture molecule or antibody), and detecting the binding of the antibody, or antigen-binding fragment thereof, to the polypeptide biomarker. The detection is generally performed using a second antibody to bind to the capture antibody complexed with its target biomarker. A target biomarker can be an entire protein, or a variant or modified form thereof. ELISA kits for the detection of biomarkers as described herein are commercially available and include pre-coated strip plates, biotinylated secondary antibody, standards, controls (where applicable), buffers, streptavidin-horse radish peroxidase (HRP), tetramethyl benzidine (TMB), stop reagents, and detailed instructions for carrying out the tests including performing standards.

In other embodiments, the levels of expression of the biomarkers are determined by quantitative real-time polymerase chain reaction.

The present disclosure also provides methods for the detection of prostate cancer in a subject wherein the levels of expression of the polypeptide biomarkers in a biological sample are determined simultaneously.

In a further aspect, the present disclosure provides compositions that can be employed in the disclosed methods. In certain embodiments, such compositions a solid substrate and a plurality of binding agents immobilized on the substrate, wherein each of the binding agents is immobilized at a different, indexable, location on the substrate and the binding agents selectively bind to a plurality of polypeptide biomarkers disclosed herein. In certain embodiments, the binding agents selectively bind to a plurality of polypeptide biomarkers comprising PSA, CRP, CHGA, BAP, CRISP3, ERG and PAP. Binding agents that can be employed in such compositions include, but are not limited to, antibodies, or antigen-binding fragments thereof. Preferably the binding agents are labeled with a detectable moiety.

In related embodiments, the present disclosure provides compositions comprising a solid substrate and a plurality of oligonucleotides immobilized on the substrate, wherein each of the oligonucleotides is immobilized at a different, indexable, location on the substrate and the oligonucleotides are specific for a plurality of polynucleotide biomarkers comprising PSA, CRP, CHGA, BAP, CRISP3, ERG and PAP.

Compositions comprising a solid substrate and a plurality of polypeptide biomarkers immobilized on the substrate are also provided, wherein each of the polypeptide biomarkers is immobilized at a different, indexable, location on the substrate and wherein the plurality of polypeptide biomarkers comprises PSA, CRP, CHGA, BAP, CRISP3, ERG and PAP.

In related aspects, the disclosed methods for determining the efficacy of a treatment for prostate cancer in a subject comprise: (a) contacting a first biological sample obtained from the subject prior to administration of the treatment with a composition disclosed herein; (b) contacting a plurality of subsequent biological samples obtained from the subject at a plurality of different, subsequent, time intervals following administration of the treatment with a plurality of compositions disclosed herein; and (c) determining changes in the levels of expression of the plurality of biomarkers following administration of the treatment. In such methods, a decrease in the level of expression of PSA and an increase in the level of expression of at least one biomarker selected from CRP, CHGA, CRISP3, ERG, BAP, and PAP that is sustained for a period of at least one or two weeks indicates that the treatment is effective in treating prostate cancer in the subject; a rapid increase in the level of expression of at least one biomarker selected from CRISP3, CRP and PAP that is sustained for a period of less than four weeks indicates that the treatment is not effective in treating prostate cancer in the subject; and an increase in the level of expression of at least one biomarker selected from CHGA, CRISP3, CRP, PAP, ERG, and BAP of less than 5%, 10% or 15% indicates that the treatment is not effective in treating prostate cancer in the subject.

In yet another aspect, the present disclosure provides compositions comprising a solid substrate and a plurality of polypeptide biomarkers disclosed herein immobilized on the substrate, wherein each of the polypeptide biomarkers is immobilized at a different, indexable, location on the substrate. In certain embodiments, the plurality of polypeptide biomarkers includes PSA, CRP, CHGA, BAP, CRISP3, ERG and PAP. Such compositions can be employed to monitor the efficacy of a treatment for prostate cancer in a subject by contacting biological samples obtained from the subject before the start of treatment and at intervals during treatment with the compositions, and determining changes in the levels of autoantibodies against the polypeptide biomarkers during the treatment regime.

In another aspect, kits for determining the efficacy of a treatment for prostate cancer in a subject are provided, such kits comprising binding agents that specifically bind to the polypeptide biomarkers disclosed herein and instructions for their use.

BRIEF DESCRIPTION OF THE DRAWINGS

FIGS. 5A and 5B depict CRP and PSA levels in A) Patient 1, and B) Patient 2 prior to and following combined treatment with ketoconazole and Leukine®.

FIGS. 6A and 6B depict CHGA and PSA levels in A) Patient 1 and B) Patient 2 prior to and following combined treatment with ketoconazole and Leukine®. The arrows depict the time of the start of treatment.

DEFINITIONS

Figure 1:
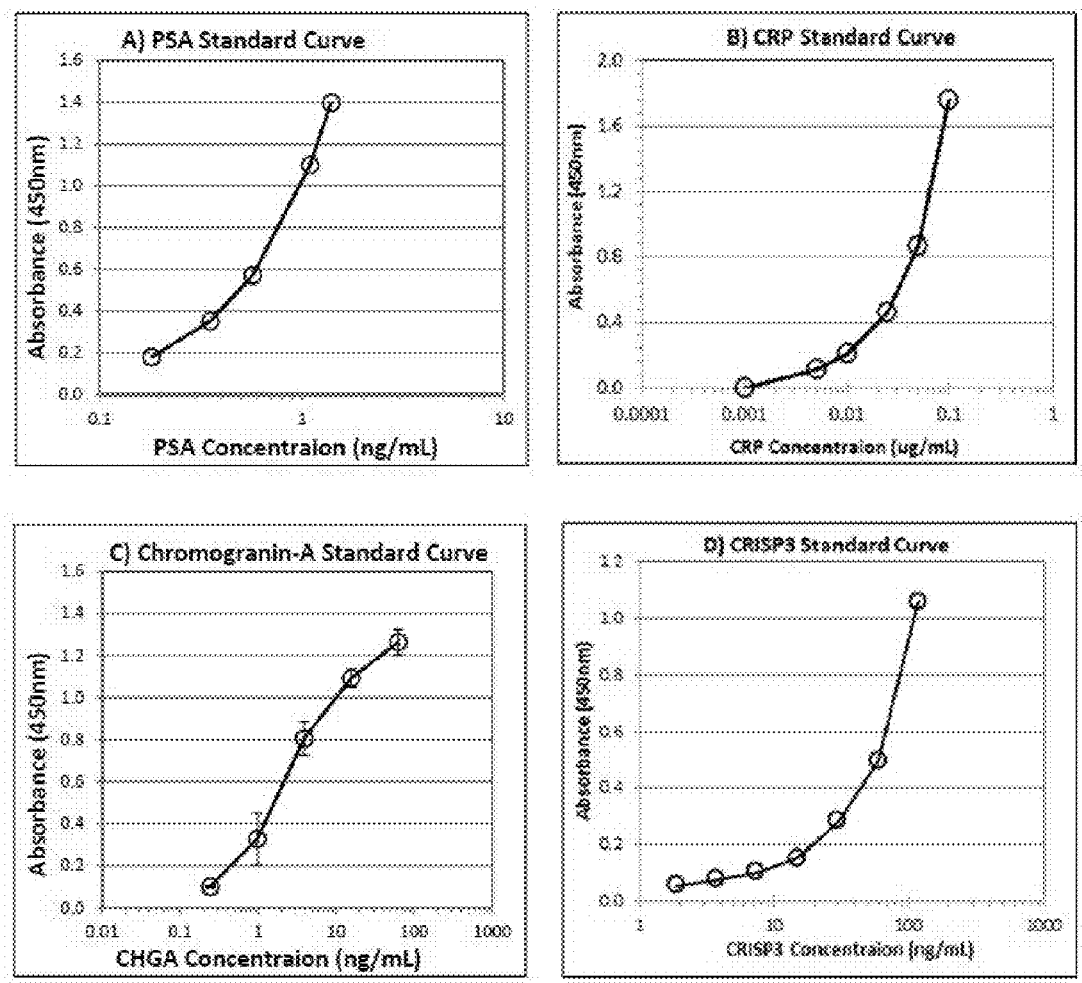
FIGS. 1A-D depict typical standard curves for A) PSA, B) CRP, C) CHGA and D) CRISP3 for quantification of enzyme linked immunoassays.

As used herein, the term "biomarker" refers to a molecule that is associated either quantitatively or qualitatively with a biological change. Examples of biomarkers include: polypeptides, proteins or fragments of a polypeptide or protein; polynucleotides, such as a gene product, RNA or RNA fragment; and other body metabolites.

As used herein, the term "antigen" refers to a synthetic peptide, polypeptide, protein or fragment of a polypeptide or protein, or other molecule which elicits an antibody response in a subject, or is recognized and bound by an antibody.

As used herein, the terms "specific binding" or "specifically binding" when used in reference to the interaction of an antibody and a protein or peptide means that the interaction is dependent upon the presence of a particular structure (i.e., the epitope) on the protein.

As used herein, the terms "binding agent specific for" or "binding agent that specifically binds" refers to an agent that binds to a polypeptide biomarker and does not significantly bind to unrelated proteins. Examples of binding agents that can be effectively employed in the disclosed methods include, but are not limited to, proteins and antibodies, such as monoclonal or polyclonal antibodies, or antigen-binding fragments thereof. In certain embodiments, the binding agent binds the polypeptide biomarker with an affinity constant of, for example, greater than or equal to about $1 \times 10^{-6}$ M.

As used herein, the term "subject" refers to a mammal, preferably a human, who may or may not have prostate cancer. Typically, the terms "subject" and "patient" are used interchangeably herein in reference to a human subject.

As used herein, the term "healthy male" refers to a male who has a PSA level in serum of less than 1.0 ng/ml, no evidence of prostate gland abnormality following a DRE and no clinical symptoms of prostatic disorders. Subjects who have no evidence of disease outside the prostate gland but whose PSA is climbing are termed "rising PSA" and subjects who are receiving no further treatments are described as being on "watchful waiting".

As used herein, the term "asymptomatic male" refers to a male who has a PSA level in serum of greater than 8 ng/ml, which is considered indicative of prostate cancer, but whose DRE is inconclusive and who has no symptoms of clinical disease.

The term "benign prostate hypertrophy" (BPH) refers to a prostatic disease with a non-malignant growth of epithelial cells in the prostate gland and the term "prostatitis" refers to another prostatic disease of the prostate, usually due to a microbial infection of the prostate gland. Both BPH and prostatitis can result in increased PSA levels.

As used herein, the term "metastatic prostate cancer" refers to prostate cancer which has spread beyond the prostate gland to a distant site, such as lymph nodes or bone.

As used herein, the term "biopsy tissue" refers to a sample of tissue (e.g., prostate tissue) that is removed from a subject for the purpose of determining if the sample contains cancerous tissue. The biopsy tissue is then examined (e.g., by microscopy) for the presence or absence of cancer.

As used herein, the term "sample" is used refers to a sample, specimen or culture obtained from any source. Biological samples include blood products (such as plasma, serum, whole blood and peripheral blood mononuclear cells (PBMCs)), urine, saliva and the like. Biological samples also include tissue samples, such as biopsy tissues or pathological tissues, that have previously been fixed (e.g., formalin, snap frozen, cytological processing, etc.).

As used herein, the term "$2^{\wedge}ddCt$ (delta delta Ct, log scale, base 2)" refers to a method for determining expression levels of genes based on the Ct value, the threshold number of cycles of amplification via the polymerase chain reaction (PCR) until the gene is detected using quantitative or real time PCR. Delta Ct is the difference in Ct between the gene of interest and a control, and ddCt is the difference between the dCt of a gene in an test sample and the dCt of the control in the test sample compared to the reference sample, (see for example Zhang et al., 2010, "ddCt Method for qRT-PCR Data Analysis", available on the BioConductor website).

As used herein, the term "predetermined threshold value of expression" of a biomarker refers to the level of expression of the same biomarker in a corresponding control/normal sample or group of control/normal samples obtained from normal, or healthy, males, i.e. males who do not have prostate cancer.

As used herein, the term "altered level of expression" of a biomarker in a test biological sample refers to a level that is either below or above the predetermined threshold value of expression for the same biomarker and thus encompasses either high (increased) or low (decreased) expression levels.

As used herein, the term "oligonucleotide specific for a biomarker" refers to an oligonucleotide that specifically hybridizes to a polynucleotide biomarker or a polynucleotide encoding a polypeptide biomarker disclosed herein, and that does not significantly hybridize to unrelated polynucleotides. In certain embodiments, the oligonucleotide hybridizes to the polynucleotide of interest under stringent conditions, such as, but not limited to, prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

As used, herein the term "polynucleotide(s)," refers to a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised.

The term "prognosis" or "providing a prognosis" refers to providing information regarding the likely impact of the presence of prostate cancer (e.g., as determined by the diagnostic methods) on a subject's future health (e.g., the risk of metastasis).

DETAILED DESCRIPTION

As outlined above, the present disclosure provides methods for monitoring treatment of prostate cancer and/or determining the efficacy of a treatment for prostate cancer in a subject by determining the levels of specific combinations of biomarkers in biological samples obtained from the subject both prior to, and during the course of, treatment.

The disclosed methods employ biomarkers selected from those shown in Table 1 below.

TABLE 1

Protein and Gene Expression Biomarkers for Monitoring Treatment of Prostate Cancer

| BIOMARKER | COMMENTS | SEQ ID NO: (AMINO ACID) |
| --- | --- | --- |
| Prostate specific antigen (PSA), also known as kallikrein 3 (KLK3) | Provides PSA levels in serum | 1-4 |
| Chromogranin A (CHGA; also referred to as CGA) | Detects prostate cancer of neuroendocrine origin; possesses calcium-binding abilities. | 5 |
| C reactive protein (CRP) | Correlates with strong inflammatory response; high levels have been associated with shorter survival and a lower probability of response to chemotherapy. | 6 |
| Cysteine-rich secretory protein 3 (CRISP3) | Androgen regulated; involved in sperm maturation | 7-9 |
| Erg | Oncogene | 10-16 |
| Bone alkaline phosphatase (BAP) | Metastatic bone cancer. There are 4 genes in the ALP gene family: intestinal, placental, germ cell and non-tissue specific. The tissue non-specific isoenzyme includes the common serum forms of ALP from bone and liver. Liver and bone ALP are isoforms of the tissue non-specific isoenzyme, differing due to post-translational glycation. | 17 |
| Kallikrein-2 (KLK2) | Serine protease with trypsin-like substrate specificity. Splits pro-PSA to create PSA; regulates KLK3 production. KLK2 and KLK3 are two of the most highly expressed genes in the prostate | 18 & 19 |
| Prostatic acid phosphatase (PAP) | Phosphatase activity in prostate. Increased amounts in men who have prostate cancer. | 20 |

The disclosed methods can be employed to determine the efficacy of treatments for prostate cancer in subjects who are undergoing androgen ablation therapy and/or in subjects who are undergoing chemotherapy including, but not limited to, subjects with metastatic prostate cancer In certain embodiments, panels of isolated prostate cancer polypeptide biomarkers are provided that include a plurality of polypeptide sequences (for example at least two, three, four, five or six sequences) selected from SEQ ID NO: 1-20. Panels of nucleic acid molecules that encode the polypeptide biomarkers disclosed herein are also provided, such panels comprising a plurality of polynucleotide sequences (for example at least two, three, four, five or six sequences) that encode the polypeptide sequences of SEQ ID NO: 1-20. In related embodiments, panels of binding agents, such as antibodies or antibody fragments, that are specific for the disclosed polypeptide biomarkers are provided, together with panels of oligonucleotides that specifically hybridize to nucleic acid molecules that encode the disclosed polypeptide biomarkers, or that specifically hybridize to the disclosed polynucleotide biomarkers.

All of the biomarkers and binding agents disclosed herein are isolated and purified, as those terms are commonly used in the art. Preferably, the biomarkers and binding agents are at least about 80% pure, more preferably at least about 90% pure, and most preferably at least about 99% pure.

In certain embodiments, the binding agents and/or oligonucleotides employed in the disclosed methods specifically bind to a variant of a polypeptide biomarker or polynucleotide biomarker disclosed herein. As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 80%, 85%, 90%, 95%, 96%, 97%, 98% or 99% identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100.

In addition to exhibiting the recited level of sequence identity, variants of the disclosed polypeptide biomarkers are preferably themselves expressed in subjects with prostate cancer at levels that are higher or lower than the levels of expression in normal, healthy individuals.

Variant sequences generally differ from the specifically identified sequence only by conservative substitutions, deletions or modifications. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptide and polynucleotide sequences may be aligned, and percentages of identical amino acids or nucleotides in a specified region may be determined against another polypeptide or polynucleotide sequence, using computer algorithms that are publicly available. The percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity.

Two exemplary algorithms for aligning and identifying the identity of polynucleotide sequences are the BLASTN and FASTA algorithms. The alignment and identity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, *Proc. Natl. Acad. Sci. USA* 85:2444-2448, 1988; and in Pearson, *Methods in Enzymol.* 183:63-98, 1990. The FASTA software package is available from the University of Virginia, Charlottesville, Va. 22906-9025. The FASTA algorithm, set to the default parameters described in the documentation and distributed with the algorithm, may be used in the determination of polynucleotide variants. The readme files for FASTA and FASTX Version 2.0x that are distributed with the algorithms describe the use of the algorithms and describe the default parameters.

The BLASTN software is available on the NCBI anonymous FTP server and is available from the National Center for Biotechnology Information (NCBI), National Library of Medicine, Building 38A, Room 8N805, Bethesda, Md. 20894. The BLASTN algorithm Version 2.0.6 [September-10-1998] and Version 2.0.11 [January-20-2000] set to the default parameters described in the documentation and distributed with the algorithm, is preferred for use in the determination of variants according to the present invention. The use of the BLAST family of algorithms, including BLASTN, is described at NCBI's website and in the publication of Altschul, et al., "Gapped BLAST and PSI-BLAST: a new generation of protein database search programs," *Nucleic Acids Res.* 25:3389-3402, 1997.

In an alternative embodiment, variant polypeptides are encoded by polynucleotide sequences that hybridize to a disclosed polynucleotide under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. An example of "stringent conditions" is pre-washing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

An "antigen-binding fragment" of an antibody refers to the part of the antibody that participates in antigen binding. The antigen binding site is formed by amino acid residues of the N-terminal variable ("V") regions of the heavy ("H") and light ("L") chains.

Antibodies may be prepared by any of a variety of techniques known to those of ordinary skill in the art (see, for example, Harlow and Lane, *Antibodies: A Laboratory Manual*, Cold Spring Harbor Laboratory, 1988). In general, antibodies can be produced by cell culture techniques, including the generation of monoclonal antibodies as described herein, or via transfection of antibody genes into suitable bacterial or mammalian cell hosts, in order to allow for the production of recombinant antibodies.

Monoclonal antibodies may be prepared using hybridoma methods, such as the technique of Kohler and Milstein (*Eur. J. Immunol.* 6:511-519, 1976), and improvements thereto. These methods involve the preparation of immortal cell lines capable of producing antibodies having the desired specificity. Monoclonal antibodies may also be made by recombinant DNA methods, such as those described in U.S. Pat. No. 4,816,567. DNA encoding antibodies employed in the disclosed methods may be isolated and sequenced using conventional procedures. Recombinant antibodies, antibody fragments, and/or fusions thereof, can be expressed in vitro or in prokaryotic cells (e.g. bacteria) or eukaryotic cells (e.g. yeast, insect or mammalian cells) and further purified as necessary using well known methods.

Antibodies may also be derived from a recombinant antibody library that is based on amino acid sequences that have been designed in silico and encoded by polynucleotides that are synthetically generated. Methods for designing and obtaining in silico-created sequences are known in the art (Knappik et al., *J. Mol. Biol.* 296:254:57-86, 2000; Krebs et al., *J. Immunol. Methods* 254:67-84, 2001; U.S. Pat. No. 6,300,064).

Digestion of antibodies to produce antigen-binding fragments thereof can be performed using techniques well known in the art. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment, which comprises both antigen-binding sites. "Fv" fragments can be produced by preferential proteolytic cleavage of an IgM, IgG or IgA immunoglobulin molecule, but are more commonly derived using recombinant techniques known in the art. The Fv fragment includes a non-covalent $V_H$::$V_L$ heterodimer including an antigen-binding site which retains much of the antigen recognition and binding capabilities of the native antibody molecule (Inbar et al., *Proc. Natl. Acad. Sci. USA* 69:2659-2662 (1972); Hochman et al., *Biochem.* 15:2706-2710 (1976); and Ehrlich et al., *Biochem.* 19:4091-4096 (1980)).

Antibody fragments that specifically bind to the polypeptide biomarkers disclosed herein can also be isolated from a library of scFvs using known techniques, such as those described in U.S. Pat. No. 5,885,793.

A wide variety of expression systems are available in the art for the production of antibody fragments, including Fab fragments, scFv, $V_L$ and $V_H$s. For example, expression systems of both prokaryotic and eukaryotic origin may be used for the large-scale production of antibody fragments. Particularly advantageous are expression systems that permit the secretion of large amounts of antibody fragments into the culture medium. Eukaryotic expression systems for large-scale production of antibody fragments and antibody fusion proteins have been described that are based on mammalian cells, insect cells, plants, transgenic animals, and lower eukaryotes. For example, the cost-effective, large-scale production of antibody fragments can be achieved in yeast fermentation systems. Large-scale fermentation of these organisms is well known in the art and is currently used for bulk production of several recombinant proteins.

Antibodies that bind to the polypeptide biomarkers employed in the present methods, together with ELISA kits that employ such antibodies for the detection of the biomarkers employed herein, are well known to those of skill in the art and are available commercially.

In certain embodiments, the expression level of one or more polypeptide biomarkers disclosed herein is determined using a binding agent, such as a protein, antibody or antibody fragment, that specifically binds to the biomarker of interest, for example in an enzyme-linked immunosorbent assay (ELISA), radioimmunoassay, antibody array, Western blot, immunohistochemical, immunoprecipitation or immunofluoresence assay. Methods for performing such assays are well known to those of skill in the art.

In one ELISA method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker is then used to detect binding of the polypeptide biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the ELISA is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in US Patent Application Publication no. US 2010/0093557 A1. Methods for the automation of immunoassays are well known in the art and include, for example, those described in U.S. Pat. Nos. 5,885,530, 4,981,785, 6,159,750 and 5,358,691.

The presence of several different biomarkers in a test sample can be detected simultaneously using a multiplex assay, such as a multiplex ELISA. Multiplex assays offers the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture antibody being positioned at a specific, pre-determined, location on the substrate. Methods for performing assays employing such arrays include those described, for example, in US Patent Application Publication nos. US 2010-0093557A1 and US 2010-0190656A1, the disclosures of which are hereby specifically incorporated by reference.

Multiplex arrays in several different formats based on the utilization of, for example, flow cytometry, chemiluminescence or electron-chemiluminesence technology, are well known in the art. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

The expression level of one or more polypeptide biomarkers in a biological sample can also be determined by mass spectrometry, in particular liquid chromatography-mass spectrometry (LC-MS) and gas chromatography-mass spectrometry (GC-MS), using methods well known to those of skill in the art.

The expression levels of one or more polynucleotide biomarkers in a biological sample can be determined, for example, using one or more oligonucleotides that are specific for the biomarker. For example, the levels of mRNA corresponding to a prostate cancer biomarker disclosed herein can be detected using oligonucleotides in Southern hybridizations, in situ hybridizations, and quantitative real-time PCR amplification (qRT-PCR). A plurality of oligonucleotides specific for a plurality of biomarkers can be employed in an array format wherein each oligonucleotide is immobilized at a pre-determined location on a substrate, such as nitrocellulose membrane. Methods for performing such assays are well known to those of skill in the art.

The oligonucleotides employed in such methods are generally single-stranded molecules, such as synthetic antisense molecules or cDNA fragments, and are, for example, 6-60 nt, 15-30 or 20-25 nt in length.

Oligonucleotides specific for a polynucleotide that encodes a polypeptide biomarker disclosed herein are prepared using techniques well known to those of skill in the art. For example, oligonucleotides can be designed using known computer algorithms to identify oligonucleotides of a defined length that are unique to the polynucleotide, have a GC content within a range suitable for hybridization, and lack predicted secondary structure that may interfere with hybridization. Oligonucleotides can be synthesized using methods well known to those in the art. For use in array formats, the oligonucleotides may be synthesized directly on the surface of a substrate. Oligonucleotides specific for the prostate cancer biomarkers disclosed herein are known in the art and are commercially available.

In certain embodiments, the oligonucleotides are labeled using one or more detectable moieties. DNA or mRNA isolated from a biological sample is contacted with the labeled oligonucleotides under conditions that allow for formation of hybridization complexes, and the amount of label associated with the hybridization complexes is measured and compared to a standard value.

In one method, the expression level of one or more prostate cancer biomarkers disclosed herein is determined by first collecting urine from a subject following DRE or prostate massage via a bicycle or exocycle. RNA is isolated from the urine sample and amplified using known techniques, such as those described by Laxman et al. (Neoplasia 2006, 8:885-8) and the expression level of mRNA corresponding to the biomarker is determined by, for example, quantitative PCR or RT-PCR using one or more oligonucleotides specific for the biomarker of interest.

For tests involving alterations in RNA expression levels, it is essential to ensure adequate standardization. Accordingly, in tests such as quantitative real time PCR or small scale oligonucleotide microarrays, at least one expression standard selected is employed.

The present disclosure further provides diagnostic panels including a plurality of binding agents (for example, antibodies) or oligonucleotides that are specific for a plurality (for example, two, three, four, five or six) of the prostate cancer biomarkers disclosed herein. In certain embodiments, such panels are in the form of arrays, or microarrays, in which the binding agents or oligonucleotides are immobilized at specific locations on a substrate. The binding agents and oligonucleotides are preferably labeled such that the size and signal intensity of each labeled complex formed between the biomarker and the binding agent/oligonucleotide are individually distinguishable. Alternatively, diagnostic panels are provided in which the biomarkers disclosed herein are immobilized at specific locations on a substrate. The biomarkers are preferably labeled such that the size and signal intensity of labeled complexes formed between the biomarkers and autoantibodies present in a biological sample are individually distinguishable. Kits comprising such diagnostic panels and instructions for their use are also provided. Such kits can also include other components required to carry out the assay, such as buffers, preservatives, wash solutions, etc.

The following examples are intended to illustrate, but not limit, this disclosure.

EXAMPLES

Methods for Examples Relating to Protein Biomarkers

Human ethics approval for the studies described herein was obtained from the Northern X Regional Ethics Committee of New Zealand. A total of 90 blood samples were obtained from subjects who were either volunteer donor healthy males or prostate cancer patients. The distribution of donors with respect to prostate disease status and age is shown in Table 2 below.

TABLE 2

Characterization of Blood Donors

| Donor status | Number of Donors | Donor Age Range |
|---|---|---|
| Healthy males | 16 | 33-72 |
| Prostatitis | 1 | 60 |
| Benign Prostatic Hyperplasia | 1 | 63 |
| Asymptomatic males | 3 | 62-69 |
| Cancer confined to prostate gland | 6 | 60-70 |
| Prostatectomy performed between 1 and 2 years prior to donating blood sample | 21 | 55-69 |
| Metastatic disease | 42 | 62-78 |

Blood samples obtained from the subjects described above were screened for levels of protein biomarkers in serum using commercially available ELISA diagnostic kits purchased from Holzel Diagnostika, Germany. Assays were performed in 96 well microtiter plates and each plate included the relevant standards supplied by the manufacturer to determine a standard curve. The linear portion of the standard curve was selected for determining scores using linear-log or log-log plots of the standard curve data. Samples for analyzes were diluted to meet the detection ranges for the ELISAs.

The protein and gene expression biomarkers selected for use in the methods disclosed herein are summarized above in Table 1. Typical standard curves for A) PSA, B) CRP, C) CHGA, and D) CRISP3 for quantification of enzyme linked immunoassays are shown in FIG. 1.

Example 1

Levels of Biomarker Expression in Different Stages of Prostate Cancer

Included in the donor samples were blood samples from 42 metastatic prostate cancer donors. We analyzed levels of PSA, KLK2, PAP, CRISP3, CRP, CGA and BAP, in each sample and then collated the data. On the basis of the results we were able to divide the metastatic prostate cancer donors into two groups, referred to as "Metastatic Group A" and "Metastatic Group B" as follows:

(i) Group A were males who had undergone hormone deprivation therapy, were considered hormone resistant and were commencing chemotherapy; and (ii) Group B were males who had undergone more extensive chemotherapy treatment and were survivors.

Distinct patterns of increased PAP, CRISP3, CRP, CGA and BAP were observed in serum from Metastatic Group A donors as compared to Metastatic Group B donors as shown in Table 3 below.

TABLE 3

Comparison of Healthy and Metastatic Group A and B Donor Samples

| | PSA ng/ml | KLK2 ng/ml | CRISP3 μg/ml | CGA ng/ml | CRP μg/ml | BAP ng/ml | PAP ng/ml |
|---|---|---|---|---|---|---|---|
| HEALTHY MALES (N = 24) | | | | | | | |
| MEAN | 0.67 | 0.35 | 2.43 | 6.68 | 10.85 | 40.16 | 4.78 |
| SE | 0.09 | 0.09 | 0.67 | 0.99 | 2.72 | 10.42 | 1.32 |

TABLE 3-continued

Comparison of Healthy and Metastatic Group A and B Donor Samples

| | PSA ng/ml | KLK2 ng/ml | CRISP3 µg/ml | CGA ng/ml | CRP µg/ml | BAP ng/ml | PAP ng/ml |
|---|---|---|---|---|---|---|---|
| METASTATIC GROUP A (DONORS N = 12) | | | | | | | |
| MEAN | 268.73 | 0.13 | 73.36 | 23.93 | 19.14 | 171.09 | 11.90 |
| SE | 86.86 | 0.04 | 16.61 | 2.29 | 3.69 | 36.86 | 4.13 |
| METASTATIC GROUP B DONORS (N = 30) | | | | | | | |
| MEAN | 2.61 | 0.19 | 39.53 | 8.56 | NT | 1.00 | 47.96 |
| SE | 0.93 | 0.10 | 8.52 | 0.88 | NT | 1.00 | 12.81 |

NT = not tested.

These data show that in Metastatic Group A samples mean PSA levels were high (268 nn/ml) while mean PAP, CRISP3, CRP, CGA and BAP levels were all increasing. There was no change in KLK2 levels. By contrast, in Metastatic Group B samples mean PSA levels were approaching normal levels (mean=2.61 ng/ml) while mean CRISP3, CRP, and BAP levels were also approaching normal. However, PAP levels remained high and there was no change in KLK2 levels.

Example 2

Monitoring Patterns of Biomarker Expression During Chemotherapy for Prostate Cancer The expression levels of various biomarkers in two prostate cancer subjects were followed as described below.

Patient 1

A 66 year old male, diagnosed 6 years previously with metastatic prostate cancer and refractory to androgen deprivation therapy, had ceased all treatment for three months. At that time his serum PSA level was 509 ng/ml. The patient commenced treatment with daily injections of 0.5 mg Leukine® and administration of 400 mg ketoconazole every eight hours. Blood samples were taken two weeks and one week prior to start of treatment, and thereafter at three weekly intervals. White cells and serum were harvested from the blood samples and analyzed as described below.

Patient 2

A 62 year old male, diagnosed 4 years previously with metastatic prostate cancer and refractory to androgen deprivation therapy, had commenced administration of 200-400 mg ketoconazole every eight hours. At that time his serum PSA level was 1086 ng/ml and rising. The patient then commenced treatment with daily injections of 0.5 mg Leukine® and administration of 400 mg ketoconazole every eight hours. Blood samples were taken immediately prior to the first injection of 0.5 mg Leukine® and thereafter at two to three weekly intervals. White cells and serum were harvested from the blood samples and analyzed as described below.

Blood Preparation

Whole blood was collected in green-topped heparin tubes. Blood was transferred to 50 mL Falcon tubes in a sterile hood, and diluted with an equal volume of sterile, pre-warmed phosphate buffered saline (PBS). Diluted blood was then carefully layered over Ficoll™, (Ficoll-Paque™; Amersham Pharmacia) at up to 30 mL diluted blood over 15 mL Ficoll™, and tubes were centrifuged at 1800 rpm for 15 min with no brake to ensure gentle deceleration.

After centrifugation, cells in the buffy coat layer at the Ficoll™ interface were harvested using a sterile disposable pipette and washed into a large volume of sterile, pre-warmed PBS. Cells were then pelleted by spinning at 1000 rpm for 5 min. Wash supernatant was discarded, cells resuspended in 10 ml sterile, pre-warmed PBS, and counted. The recovered cell yield was $1 \times 10^6$ cells/ml of whole blood collected.

Patient Monitoring During Treatment with Leukine® and Ketoconazole

Figure 2:
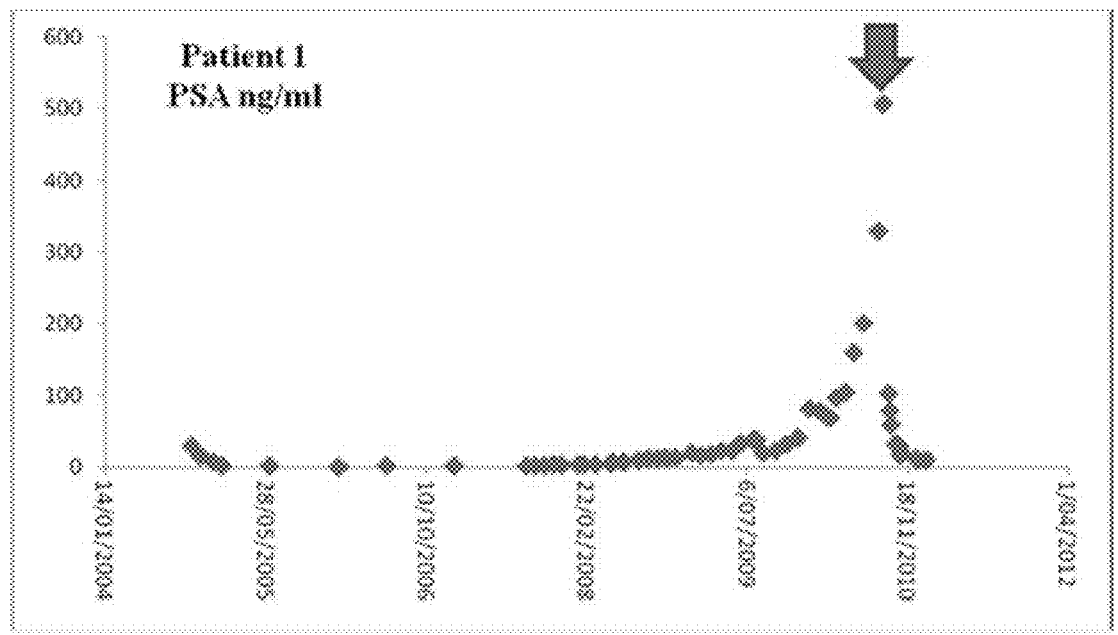
FIG. 2 depicts Patient 1 PSA levels prior to and following combined treatment with ketoconazole and Leukine®. The arrow depicts the time of the start of treatment.
Figure 3:
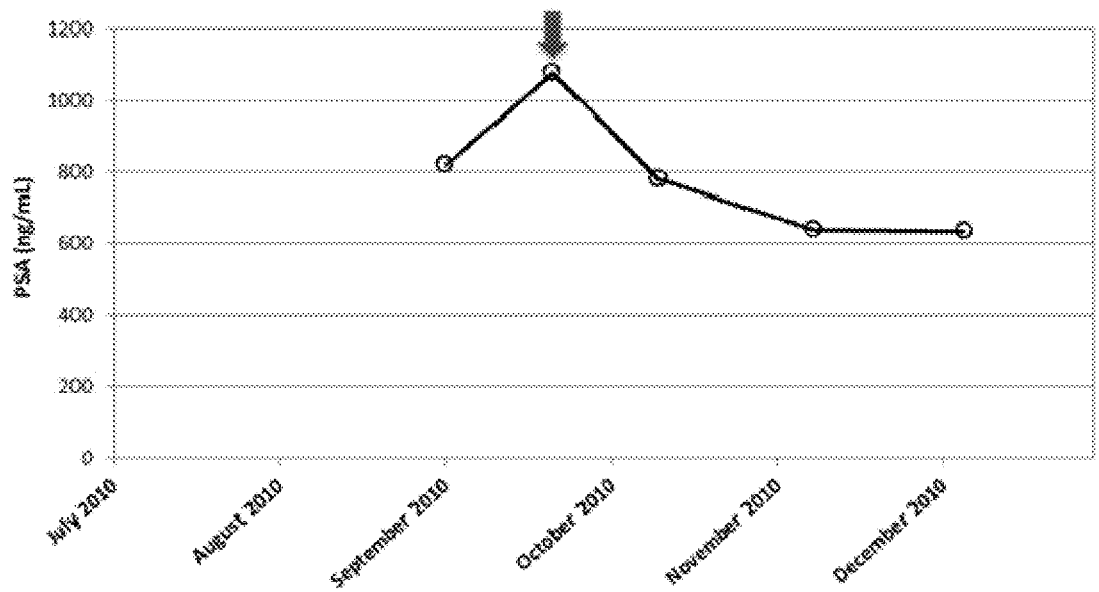
FIG. 3 depicts Patient 2 PSA levels prior to and following combined treatment with ketoconazole and Leukine®. The arrow depicts the time of the start of treatment.

After 4 months of treatment with Leukine® and ketoconazole, the PSA levels of Patient 1 had decreased from 509 to 9.8 ng/ml. The time course of changing serum prostate antigen levels in Patient 1 both before and after treatment with Leukine® and ketoconazole is shown in FIG. 2, with the arrow showing the start of treatment. By contrast, after treatment the PSA levels of Patient 2 had decreased from 1086 to 650 ng/ml and showed no further decrease (FIG. 3). These patients thus appeared to have different responder phenotypes to the treatment regime.

To expand upon the differences in biomarker levels seen in serum samples from Group A and Group B metastatic prostate cancer donors, Patients 1 and 2 were bled at 2-3 week intervals, and CRISP3, CRP and CHGA levels were measured.

Figure 4A:
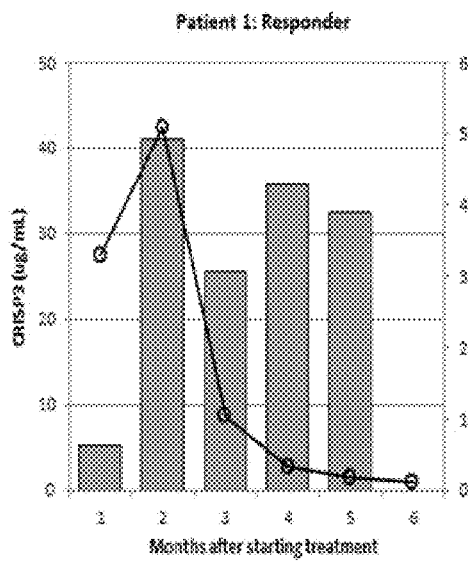
FIGS. 4A and 4B depict changes in serum levels of CRISP3 in two patients with metastatic prostate cancer (referred to as Patient 1 and Patient 2, respectively) prior to and during treatment with ketoconazole and Leukine®.
Figure 4B:
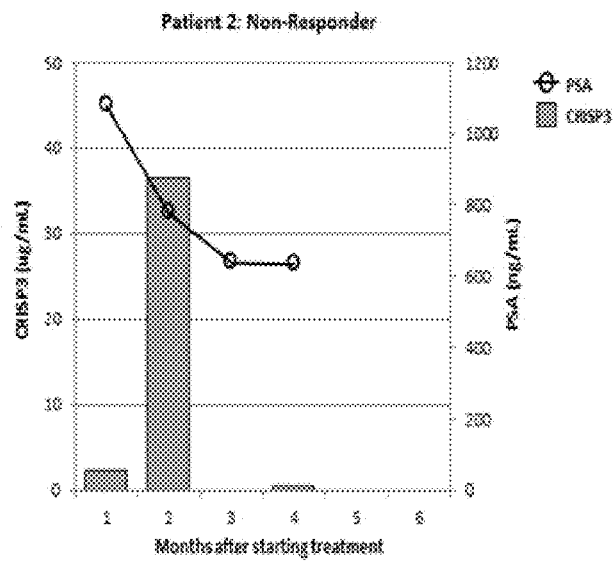

The data in FIGS. 4A and 4B compares changes in serum levels of CRISP3 in Patient 1 and Patient 2, respectively. A distinct difference was seen in CRISP3 levels between these two patients. Specifically, Patient 1 exhibited increased CRISP3 levels which were sustained for the course of the study and correlated with the significant decrease in PSA levels. Patient 2 exhibited a rapid increase in CRISP3 levels which rapidly disappeared and, in this case, correlated with a much smaller decrease in PSA levels.

FIGS. 5A and 5B depict CRP and PSA levels in Patient 1 and Patient 2, respectively, following combined treatment with ketoconazole and Leukine®. A distinct difference was seen in CRP levels between these two patients. Patient 1 exhibited increased CRP levels which were sustained for the course of the study, and correlated with the significant decrease in PSA levels. In contrast, Patient 2 exhibited a rapid increase in CRP levels which rapidly disappeared and, in this case, correlated with a much smaller decrease in PSA levels.

FIGS. 6A and 6B depict similar trends in CHGA and PSA levels in Patients 1 and 2 following combined treatment with ketoconazole and Leukine®. Patient 1 exhibited increased CHGA levels which were sustained for the course of the study, and correlated with the significant decrease in PSA levels. CHGA levels for Patient 2 did not increase above the background sensitivity of the ELISA, which was less than 0.3 ng/ml. Again, these data supported the interpretation that these patients appeared to have different responder phenotypes to the treatment regime.

Figure 7A:
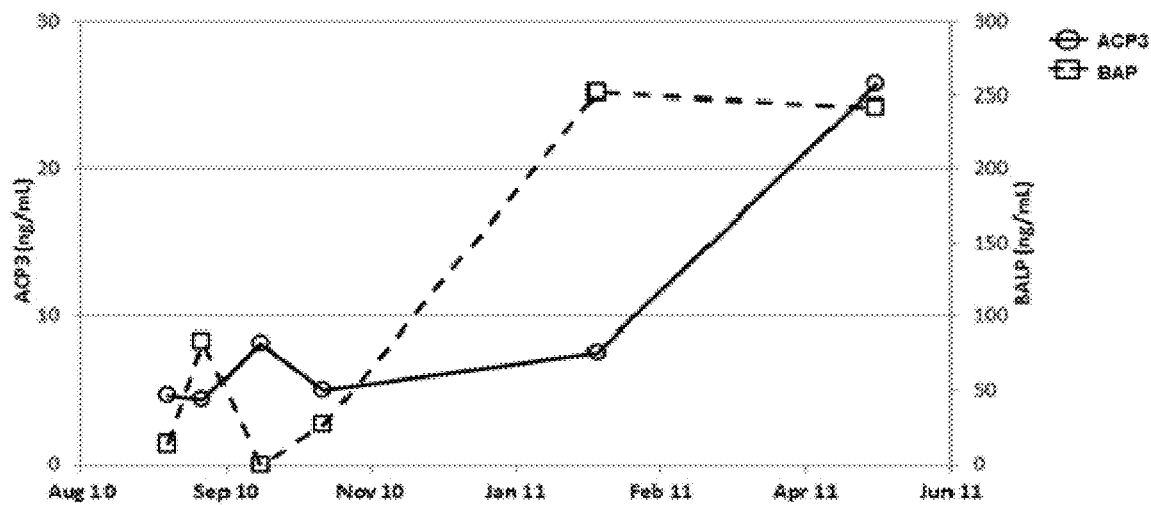
FIGS. 7A and 7B depict changes in serum levels of PAP and BAP (referred to as ACP3) in Patients 1 and 2, respectively, prior to and following combined treatment with ketoconazole and Leukine®.
Figure 7B:
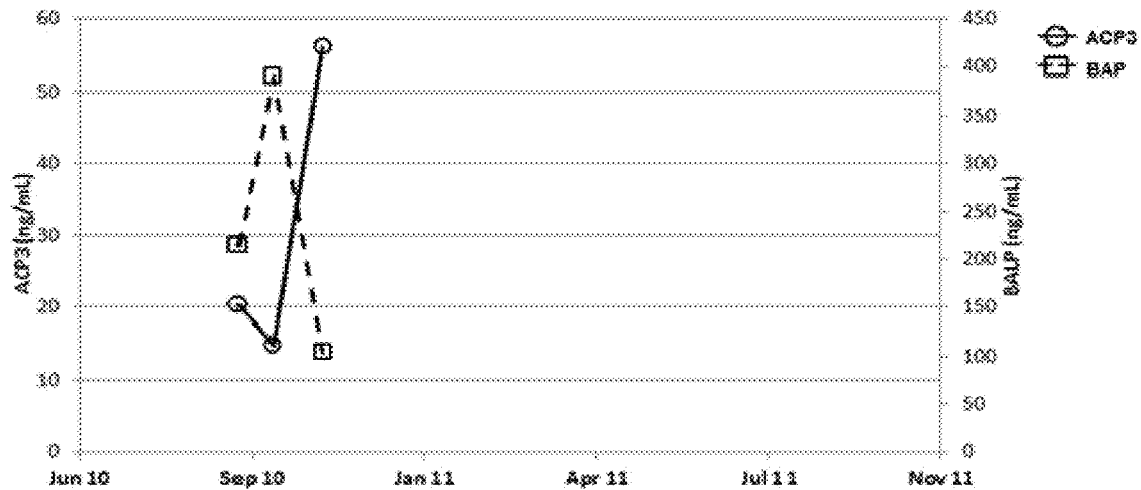

The data in FIGS. 7A and 7B compares changes in serum levels of PAP (referred to in FIGS. 7A and B as ACP3) and BAP in Patients 1 and 2, respectively. Patient 1 exhibited increased PAP and BAP levels which were sustained for the course of the study correlated with the significant decrease in PSA levels. Patient 2 exhibited an initial increase in PAP levels then a decrease, similar to the trend in biomarkers CRP, CHGA and CRISP3.

In summary, the two patients showed different response phenotypes during treating with Leukine® and ketoconazole. Specifically, Patient 1 exhibited increased CRISP3, CRP, and CHGA levels which were sustained for the course of the study and correlated with the significant decrease in PSA levels. In contrast, Patient 2 showed a sharp, transient elevation of CRISP3 and CRP after the start of treatment, while the levels of CHGA for this patient did not increase above the background sensitivity of the ELISA, and the decrease in PSA levels was small. CRISP3 and CRP both have properties of acute phase proteins, with innate immune cells producing CRISP3 and adaptive immune cells producing CRP. Inflammatory mediators stimulate the production of CHGA from neuroendocrine cells, with CHGA being a neuroendocrine biomarker. One possible interpretation of these results is that the immune system of Patient 2 was severely impaired while the immune system of Patient 1 was more active.

Patient 1 exhibited increased PAP and bone alkaline phosphatase (BAP) levels which were sustained for the course of the study correlated with the significant decrease in PSA levels. Patient 2 exhibited an initial increase in PAP levels then a decrease similar to the trend in biomarkers CRISP3, CRP and CGA. PAP increases in metastatic cancer during treatment and is a biomarker for residual prostate cancer cells. BAP is released during bone damage and healing and is indicative that bone lesions are being destroyed.

Patient Monitoring During Docetaxel Treatment

Following seven months of treatment with ketoconazole and Leukine® treatment, Patient 1 was rested for five weeks and then commenced treatment with Docetaxel, dexamethasone and prednisolone, following a three week cycle. The patient received six cycles of docetaxel treatment and then treatment was stopped. Blood samples were taken at the start of treatment and then at monthly intervals, and the levels of the biomarkers PAP, CRISP3, CRP and BAP were determined.

Figure 8:
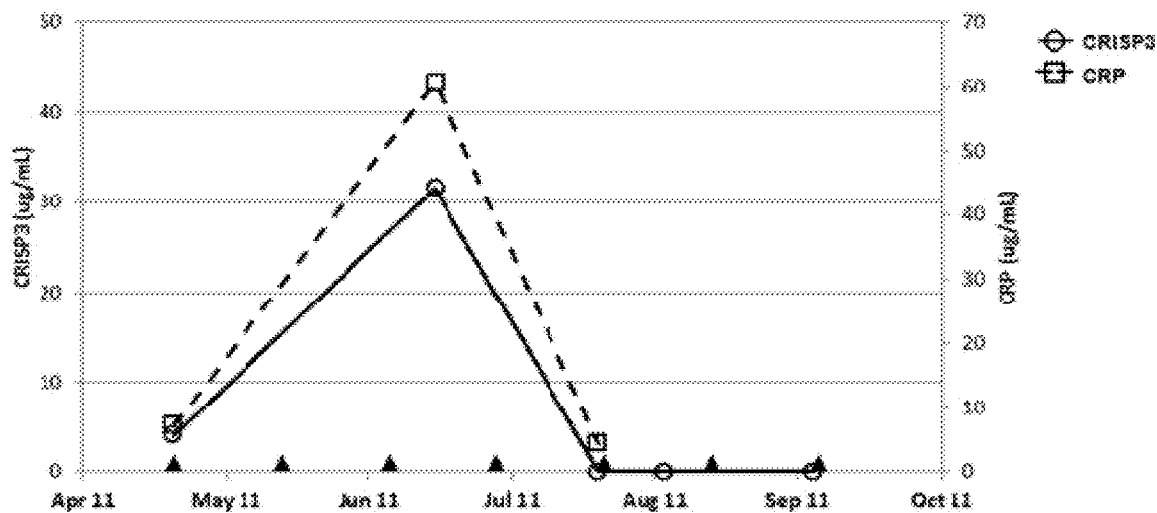
FIG. 8 depicts changes in CRISP3 and CRP serum levels in Patient 1 during treatment with Docetaxel, dexamethasone and prednisolone.
Figure 9:
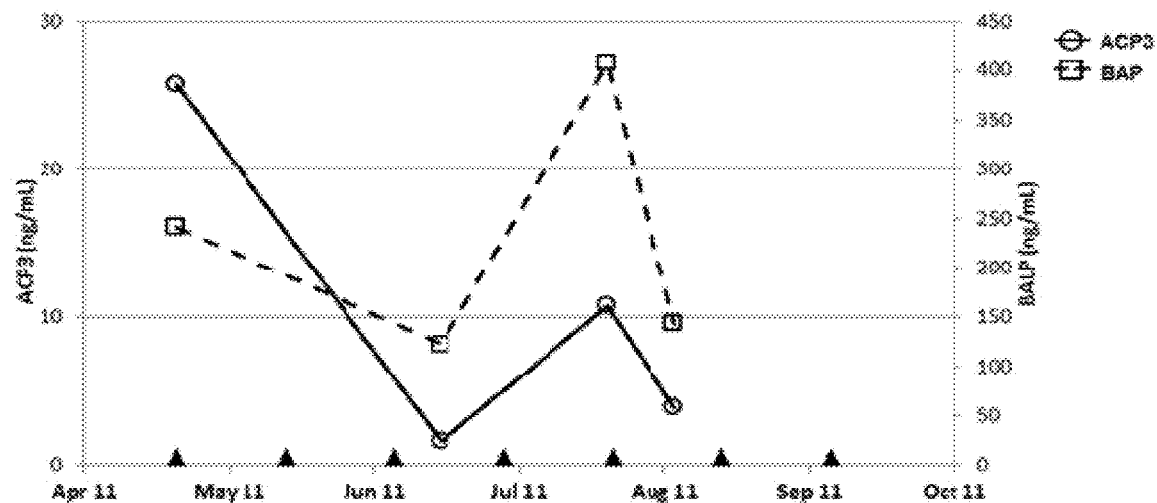
FIG. 9 depicts changes in PAP (referred to as ACP3) and BAP serum levels in Patient 1 during treatment with Docetaxel, dexamethasone and prednisolone.

The data of FIG. 8 shows that, following start of treatment, an increase in CRISP3 and CRP serum levels for three cycles of chemotherapy was observed followed by a decrease. By cycle four, serum levels of both CRISP3 and CRP had reached background and showed no further increase. The data of FIG. 9 shows that, following start of treatment, there was a gradual drift downwards of PAP (referred to in the figure as ACP3) and BAP serum levels and no increase above starting levels was observed.

The decrease in CRISP3 and CRP levels is indicative of the immune system (and perhaps liver) being slowly degraded by continuing chemotherapy and not recovering in three weeks. This profile indicates that treatment beyond four cycles is not beneficial to the patient. There was a gradual drift downwards of PAP and BAP serum levels that showed no increase above starting levels. BAP indicates bone repair is ceasing and there are reports that PAP levels generally accompany metastatic prostate cancer cells.

Methods for Examples Relating to Gene Expression Biomarkers

Gene expression analyses were performed using PBMCs from a group of 15 prostate cancer patients and five healthy subjects (three males and two females). The healthy males were determined to be free of prostate cancer and showed no evidence of prostate cancer in a 12 month follow up. Blood was collected at different times over a four month period. The collection times of specific donor samples are shown in Table 4, together with an internal code, gender and disease status (CaP=prostate cancer; Norm=healthy subject; dates shown as day/month/year).

TABLE 4

Blood collection from healthy (Normal) and prostate cancer (CaP) subject at different times

| Code | Gender | Status | 12 Aug. 2010 | 9 Sep. 2010 | 21 Sep. 2010 | 11 Oct. 2010 | 2 Nov. 2010 | 9 Nov. 2010 | 29 Nov. 2010 | 7 Dec. 2010 | 4 Feb. 2011 |
|---|---|---|---|---|---|---|---|---|---|---|---|
| 1 | male | CaP | x | x | x | x | x | | x | | x |
| 2 | male | CaP | | x | | | | | | | |
| 3 | male | Normal | x | x | x | x | x | | x | x | |
| 4 | male | Normal | x | x | | | | | x | | |
| 5 | male | CaP | | x | | | | | | | |
| 6 | male | CaP | | x | | | | | | | |
| 7 | female | Normal | | x | | | | | | | |
| 8 | female | Normal | | x | | | | | | | |
| 9 | female | CaP | x | x | | | | | | | |
| 10 | male | CaP | | x | | | | | | | |
| 11 | male | CaP | x | x | | | | | | | |
| 12 | male | Cap | | x | | | | | | | |
| 13 | male | CaP | | x | | | | | | | |
| 14 | male | CaP | | x | | | | | | | |
| 15 | male | CaP | x | | | | | | | | |
| 16 | male | CaP | x | | x | x | x | | | x | x |
| 17 | male | CaP | x | | | | | | | | |
| 18 | male | CaP | | | x | x | | x | | x | |
| 19 | male | Normal | | | | | | | x | | |
| 20 | male | CaP | | | | | | | | | x |

PBMCs were purified by centrifugation over a layer of Ficoll™ Hypaque and RNA extractions using recovered cells were all performed with TRIZOL™ (Invitrogen, Cat#15596-026), according to the manufacturer's instructions. cDNA amplifications were performed with SuperScript VILO cDNA Synthesis Kit (Invitrogen, Cat#11754-250) containing (10x) SuperScript Enzyme Mix and (5x) VILO Reaction Mix. Briefly, 10 µl of the sample (10 ng/µl final concentration) was added to a PCR tube strip. The master mix was prepared according to the manufacturer's protocol and 10 µl of the master mix was added, mixed by vortexing for a few seconds and centrifuged at 1,000 rpm for a few seconds. Amplification involved the following steps: 10 minutes at 25° C.; 60 minutes at 42° C.; 5 minutes at 85° C.; held at 4° C. Storage of the cDNA was at −20° C.

Quantitative Real Time PCR amplification employed INVITROGEN PLATINUM™ SYBR® Green qPCR Super-Mix-UDG with ROX (Cat. no. 11744-500). Briefly, cDNA samples retrieved from −20° C. were tested in triplicate. Samples were briefly centrifuged, diluted 1:5 with RNase free water, mixed and centrifuged. 2 µl of each cDNA was transferred to appropriate wells of a 384-well microtiter plate. For a single reaction, 5 µl of Syber green master mix plus 0.2 µl of 10 μM forward and reverse specific primers plus were mixed with 2.6 μl of RNase free water. Then 8 μl of each master mix was transferred to appropriate assays in microwells and the plates sealed with optical plastic. After mixing by vortexing, the plates were centrifuged briefly, and then analyzed via qRT-PCR (7900 HT fast Real Time PCR System, Applied Biosystems).

Conditions used for qRT-PCR are described in Table 5, below, and the oligonucleotide primers investigated are depicted in Table 6.

TABLE 5

Conditions used for qRT-PCR

| Programme | Number | Dissociation step | Number |
|---|---|---|---|
| 50° C. × 2 min. | 1 | 95° C. × 15 sec. | |
| 95° C. × 2 min. | 1 | 60° C. × 15 sec. | 1 |
| 95° C. × 15 sec. | 40 | 95° C. × 15 sec. | |
| 60° C. × 1 min. | | | |

TABLE 6

Primers Employed

| qRT Primers | Supplier | Catalog No. (Forward/Reverse) | qRT Primers | Supplier | Catalog No. (Forward/Reverse) |
|---|---|---|---|---|---|
| CRISP3 | Invitrogen | V4154C05/V4154C06 | PEX10 | Invitrogen | V4153D01/V4153D02 |
| ERG | IDT* | 60992473/60992474 | SIM2 | IDT* | 61006528/61006529 |

*IDT = Integrated DNA Technologies

Example 3

Monitoring CRISP3 mRNA Expression in Prostate Cancer Patients During Treatment with Ketoconazole and Leukine®

The level of CRISP3 mRNA expression was followed in three prostate cancer subjects (patient 1 (donor code 1), patient 2 (donor code 18) and patient 3 (donor code 16)) and one healthy male subject. Patients 1 and 2 are described above in Example 1.

Patient 3 (Donor Code 16)

A 62 year old male, diagnosed 3 years previously with prostate cancer, had a prostatectomy 6 months after diagnosis and had received intermittent androgen deprivation therapy. At the start of the study the prostatectomy had taken place two and a half years previously and his PSA levels were less than 0.1 ng/ml where they remained for the duration of the study. This patient was not treated during the duration of the monitoring described below.

Healthy Control Subject

Blood samples were taken from a healthy 40 year old male donor with a PSA level of less than 0.1 ng/ml before and through the duration of the study.

The expression of CRISP3 mRNA was analyzed in Patient 1 from before treatment (12 Aug. 2010), the start of treatment being 5 Sep. 2010; in Patient 2 from 21 Sep. 2010, which was immediately prior to the start of combined Leukine®/ketoconazole treatment; and in Patient 3, who was not treated with any regime, from 12 Aug. 2010.

Figure 10:
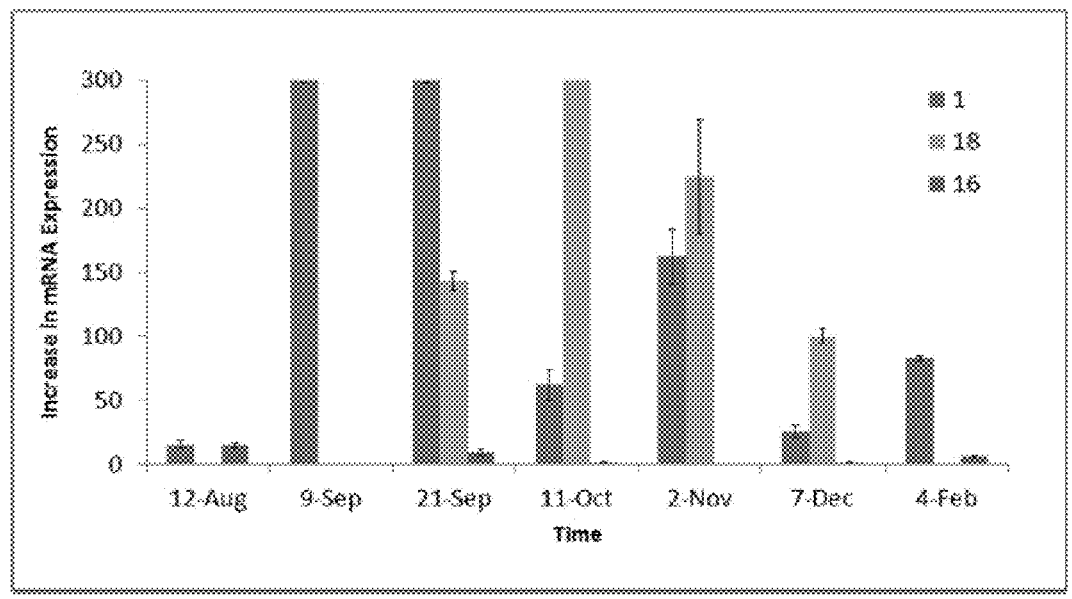
FIG. 10 depicts CRISP3 mRNA expression in PBMCs from normal and prostate cancer subjects at multiple time points.

Blood samples were collected over the period 12 Aug. 2010 to 4 Feb. 2011. Quantitative real time PCR analysis of samples collected at different times showed an increase in expression of CRISP3 mRNA in Patients 1 and 2 (donor codes 1 and 18, respectively) but not in Patient 3 (donor code 16) over the observed period (see FIG. 10 and Table 7; compare 2^ddCt values for samples 1 and 18 with 2^ddCt value of sample 16). The samples were normalized on GAPDH and compared with the negative control value of normal donor 03. In Table 7, the 2^ddCt value of two more healthy donors 4 and 19 were added to give more background information on CRISP3 levels in normal subjects.

TABLE 7

CRISP3 mRNA expression in healthy (normal) and prostate cancer (CaP) subjects

| CaP Donor | | | CRISP3 mRNA | |
|---|---|---|---|---|
| Code | Status | Date | $2^{-ddCt}$ | error bars |
| 1 | CaP | August 12 | 15.87 | 2.73 |
| | | September 9 | 923.98 | 25.57 |
| | | September 21 | 323.58 | 25.46 |
| | | October 11 | 62.37 | 12.05 |
| | | November 2 | 162.56 | 21.84 |
| | | December 7 | 26.09 | 4.80 |
| | | February 4 | 82.87 | 2.22 |
| 16 | CaP | August 12 | 15.13 | 2.16 |
| | | September 9 | / | / |
| | | September 21 | 9.63 | 2.36 |
| | | October 11 | 1.56 | 0.56 |
| | | November 2 | / | / |
| | | December 7 | 1.90 | 0.30 |
| | | February 4 | 6.48 | 1.07 |
| 18 | CaP | August 12 | / | / |
| | | September 9 | / | / |
| | | September 21 | 143.32 | 7.01 |
| | | October 11 | 442.23 | 83.33 |
| | | November 2 | 224.72 | 44.95 |
| | | December 7 | 100.41 | 6.02 |
| | | February 4 | / | / |
| 4 | Normal | August 12 | 14.73 | 0.90 |
| | | September 9 | 8.03 | 0.92 |
| 19 | Normal | November 2 | 8.21 | 6.24 |

Figure 11:
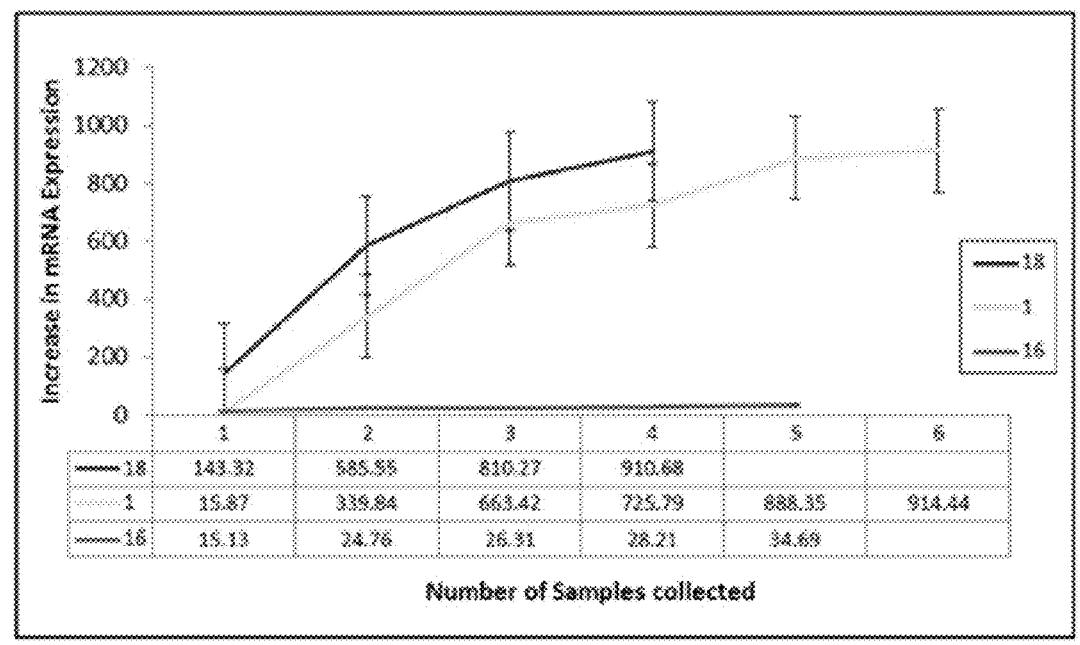
FIG. 11 depicts a summary of increases in CRISP3 mRNA expression in prostate cancer subjects over time.

A summary of CRISP3 expression from Patients 1 to 3 is shown in FIG. 11 where the total increase in expression of CRISP3 for each patient's samples collected over the study from 12 Aug. 2010 to 4 Feb. 2011 are shown. The samples were normalized on GAPDH. To summarize, both Patients 1 and 2 showed significant increases in CRISP3 RNA expression after treatment with ketoconazole and Leukine®, indicating that ketoconazole and/or Leukine® were involved in stimulating the CRISP3 gene.

Example 4

Monitoring ERG mRNA Expression in Prostate Cancer Patients Treated with Ketoconazole and Leukine®

Figure 12:
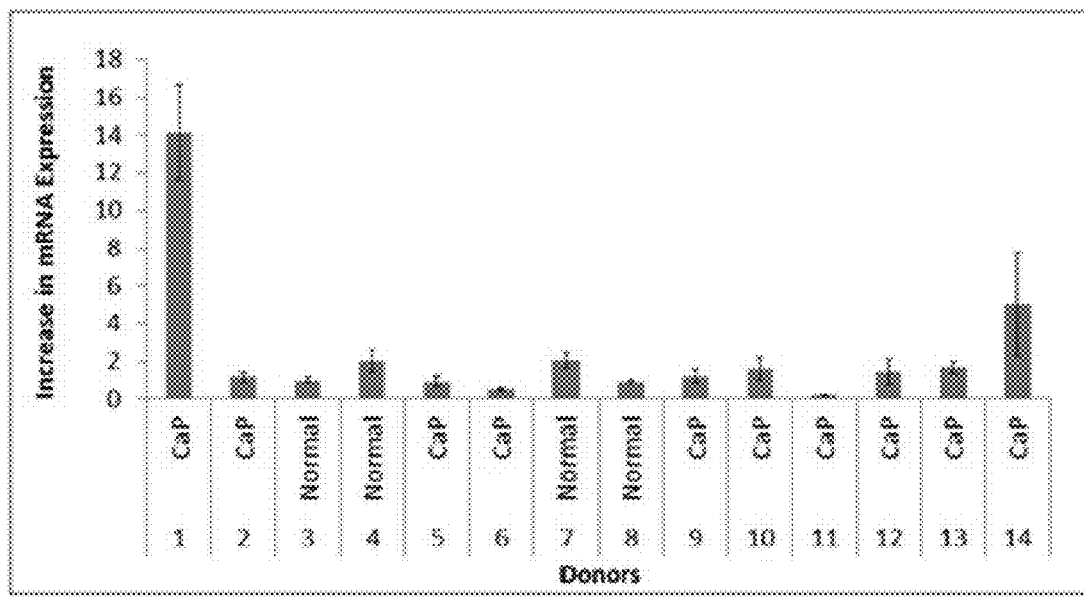
FIG. 12 depicts ERG mRNA expression in PBMCs from normal (Normal) and prostate cancer (CaP) subjects.

ERG gene expression has been reported to be common to many prostate cancers. Quantitative real time PCR analysis for expression of ERG mRNA was performed on a set of blood samples collected at the same time point (9 Sep. 2010) from a number of prostate cancer subjects and normal donors. The results showed a unique expression pattern with a significantly increased level of expression of ERG in Patient 1 (donor code 1) compared to the other donors collected at the same time point (see FIG. 12 and Table 8, compare sample code 1, 2^ddCt value 14.14+/−2.53 with 2^ddCt value samples 2 to 14). The samples are normalized on GAPDH and compared with the negative control value 03 (yellow highline).

TABLE 8

ERG mRNA expression in healthy (normal) and prostate cancer subjects.

| ERG mRNA Expression Normalized on Donor 3 | | | |
|---|---|---|---|
| | | Sep. 9, 2010 | |
| Code | Status | 2^-ddCt | error bars |
| 1 | CaP | 14.14 | 2.53 |
| 2 | CaP | 1.16 | 0.29 |
| 3 | Normal | 1.00 | 0.17 |
| 4 | Normal | 2.02 | 0.59 |
| 5 | CaP | 0.92 | 0.26 |
| 6 | CaP | 0.52 | 0.10 |
| 7 | Normal | 2.07 | 0.42 |
| 8 | Normal | 0.91 | 0.07 |
| 9 | CaP | 1.19 | 0.34 |
| 10 | CaP | 1.63 | 0.59 |
| 11 | CaP | 0.20 | 0.04 |
| 12 | CaP | 1.45 | 0.66 |
| 13 | CaP | 1.69 | 0.32 |
| 14 | CaP | 5.02 | 2.73 |

Figure 13:
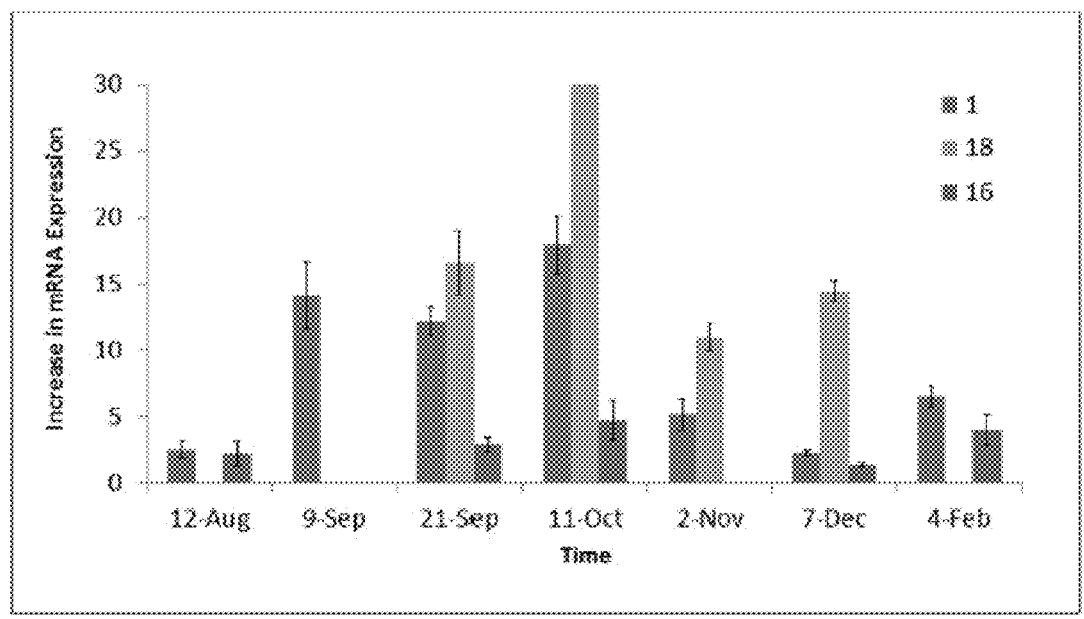
FIG. 13 depicts ERG mRNA expression in PBMCs from normal and prostate cancer subjects at various times.

In order to assess the effect of treatment with ketoconazole and Leukine® on the expression of ERG mRNA in Patients 1, 2 and 3, samples were collected as described above from 12 Aug. 2010 to 4 Feb. 20101 and analyzed by quantitative real time PCR for levels of ERG RNA. The samples collected at different times showed a significant increase of the mRNA level of ERG in Patients 1 and 2 (donor codes 1 and 18, respectively) compared to no changes in Patient 3 (donor code 16) who received no ketoconazole/Leukine® treatment. The higher ERG expression of Patient 1 showed a reduction to a baseline expression levels over the course of several months, matching with the expression level of Patient 2 (see FIG. 13 and Table 9, compare 2^ddCt value samples 1 and 18 with sample 16), and with the expression level in the healthy donors (Table 9, compare 2^ddCt value samples 1, 18 and 16 with samples 4 and 19). The samples were normalized on GAPDH and compared with the negative control value of donor 03. Table 9 includes the relative value of two normal donors, 4 and 19, to illustrate background ERG mRNA levels.

TABLE 9

ERG mRNA expression in healthy (normal) and prostate cancer subjects

| CaP Donor | | | ERG mRNA | |
|---|---|---|---|---|
| Code | Status | Date | $2^{-ddCt}$ | error bars |
| 1 | CaP | August 12 | 2.52 | 0.64 |
| | | September 9 | 14.14 | 2.53 |
| | | September 21 | 12.18 | 1.09 |
| | | October 11 | 17.92 | 2.20 |
| | | November 2 | 5.14 | 1.15 |
| | | December 7 | 2.30 | 0.18 |
| | | February 4 | 6.51 | 0.82 |
| 16 | CaP | August 12 | 2.26 | 0.92 |
| | | September 9 | / | / |
| | | September 21 | 2.93 | 0.55 |
| | | October 11 | 4.74 | 1.43 |
| | | November 2 | / | / |
| | | December 7 | 1.40 | 0.20 |
| | | February 4 | 4.01 | 1.13 |
| 18 | CaP | August 12 | / | / |
| | | September 9 | / | / |
| | | September 21 | 16.59 | 2.42 |
| | | October 11 | 81.18 | 14.07 |
| | | November 2 | 10.59 | 1.00 |
| | | December 7 | 14.46 | 0.80 |
| | | February 4 | / | / |
| 4 | Normal | August 12 | 5.62 | 0.43 |
| | | September 9 | 2.02 | 0.59 |
| 19 | Normal | November 2 | 1.01 | 0.77 |

Figure 14:
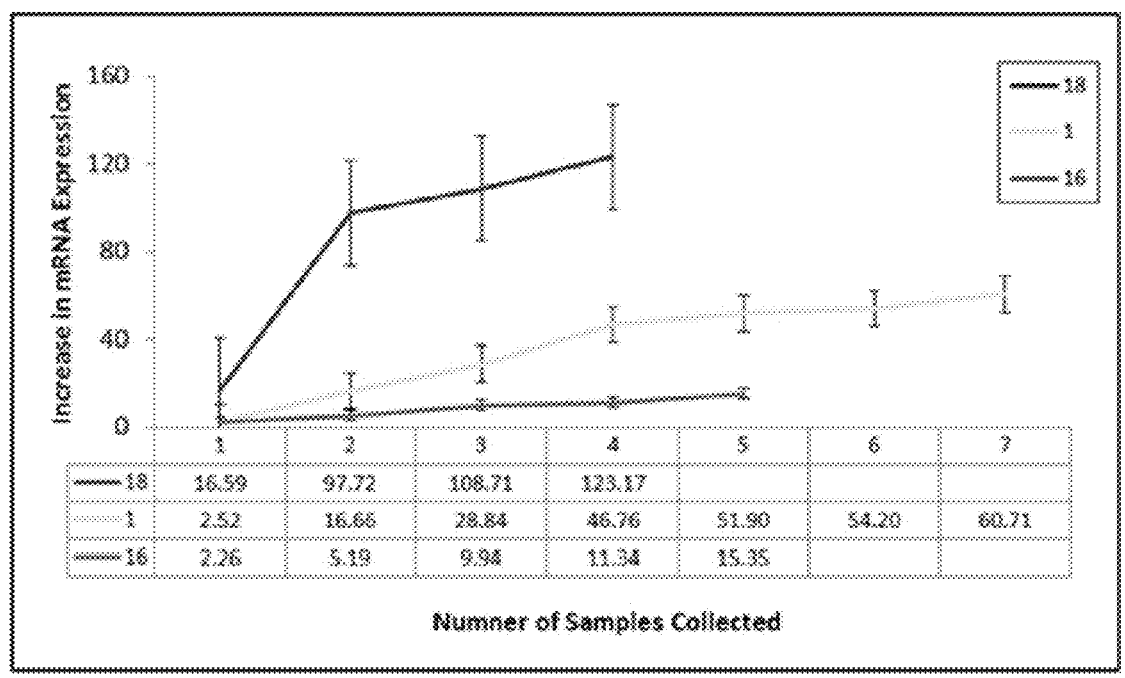
FIG. 14 depicts a summary of increases in ERG mRNA expression in PBMCs from normal and prostate cancer subjects over time.

FIG. 14 shows the relative increase in expression of the ERG mRNA individually for Patients 1, 2 and 3 over the duration of the study. All the data was normalized on the ct value of normal donor 3.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

SEQ ID NO: 1-20 are set out in the attached Sequence Listing. The codes for nucleotide sequences used in the attached Sequence Listing, including the symbol "n," conform to WIPO Standard ST.25 (1998), Appendix 2, Table 1.

The invention claimed is:

1. A composition comprising a solid substrate and a plurality of binding agents immobilized on the substrate, wherein each of the binding agents is immobilized at a different, indexable, location on the substrate and the binding agent specifically bind to a plurality of polypeptide biomarker, the plurality of polypeptide biomarker comprising:
   a) at least one sequence selected from SEQ ID NOs: 1-4;
   b) SEQ ID NO:5;
   c) SEQ ID NO: 6;
   d) at least one sequence selected from SEQ ID NO: 7-9;
   e) at least one sequence selected from SEQ ID NO: 10-16;
   f) SEQ ID NO: 17; and
   g) SEQ ID NO: 20.

2. The composition of claim 1, wherein the binding agents are antibodies, or antigen-binding fragments thereof.

3. The composition of claim 1, wherein the binding agents are labeled with a detectable moiety.

4. A composition comprising a solid substrate and a plurality of polypeptide biomarkers immobilized on the substrate, wherein each of the polypeptide biomarker is immobilized at a different, indexable, location on the substrate and wherein the plurality of polypeptides biomarkers comprises:
   a) at least one sequence selected from SEQ ID NOs: 1-4;
   b) SEQ ID NO:5;
   c) SEQ ID NO: 6;
   d) at least one sequence selected from SEQ ID NO: 7-9;
   e) at least one sequence selected from SEQ ID NO: 10-16;
   f) SEQ ID NO: 17; and
   g) SEQ ID NO: 20.

5. A composition comprising a solid substrate and a plurality of oligonucleotides immobilized on the substrate, wherein each of the oligonucleotides is immobilized at a different, indexable, location on the substrate and the oligonucleotides are specific for a plurality of polynucleotide biomarkers comprising nucleotide sequences encoding:
   a) at least one sequence selected from SEQ ID NOs: 1-4;
   b) SEQ ID NO:5;
   c) SEQ ID NO: 6;
   d) at least one sequence selected from SEQ ID NO: 7-9;
   e) at least one sequence selected from SEQ ID NO: 10-16;
   f) SEQ ID NO: 17; and
   g) SEQ ID NO: 20.

6. The composition of claim 3, wherein the detectable moiety is selected from the group consisting of: cheminescent and luminescent agents; radioisotopes; colorimetric agents; and enzyme-substrate labels.

7. The composition of claim 4, wherein the polypeptide biomarkers are labeled with a detectable moiety.

8. The composition of claim 7, wherein the detectable moiety is selected from the group consisting of: cheminescent and luminescent agents; radioisotopes; colorimetric agents; and enzyme-substrate labels.

* * * * *